US009938571B2

(12) United States Patent
Battrell et al.

(10) Patent No.: US 9,938,571 B2
(45) Date of Patent: *Apr. 10, 2018

(54) COMPOSITIONS AND METHODS FOR DEHYDRATED STORAGE OF ON-BOARD REAGENTS IN MICROFLUIDIC DEVICES

(71) Applicant: Micronics, Inc., Redmond, WA (US)

(72) Inventors: C. Frederick Battrell, Wenatchee, WA (US); Denise Maxine Hoekstra, Monroe, WA (US); Joan Haab, Seattle, WA (US); John R. Williford, Sammamish, WA (US); Sabrina N. Gunderson, Bellevue, WA (US); Elizabeth R. Leber, Seattle, WA (US); Isaac Sprague, Kirkland, WA (US)

(73) Assignee: Micronics, Inc., Redmond, WA (US)

( * ) Notice: Subject to any disclaimer, the term of this patent is extended or adjusted under 35 U.S.C. 154(b) by 85 days.

This patent is subject to a terminal disclaimer.

(21) Appl. No.: 14/554,720

(22) Filed: Nov. 26, 2014

(65) Prior Publication Data
US 2015/0152481 A1 Jun. 4, 2015

Related U.S. Application Data

(60) Division of application No. 13/323,684, filed on Dec. 12, 2011, now Pat. No. 8,921,085, which is a continuation of application No. PCT/US2010/038141, filed on Jun. 10, 2010.

(60) Provisional application No. 61/186,442, filed on Jun. 12, 2009.

(51) Int. Cl.
C12Q 1/68 (2006.01)

(52) U.S. Cl.
CPC ........... C12Q 1/686 (2013.01); C12Q 1/6806 (2013.01)

(58) Field of Classification Search
None
See application file for complete search history.

(56) References Cited

U.S. PATENT DOCUMENTS

| | | |
|---|---|---|
| 4,206,200 A | 6/1980 | Guthöhrlein et al. |
| 4,457,916 A | 7/1984 | Hayashi et al. |
| 4,762,857 A | 8/1988 | Bollin, Jr. et al. |
| 4,891,319 A | 1/1990 | Roser |
| 5,098,893 A | 3/1992 | Franks et al. |
| 5,200,399 A | 4/1993 | Wettlaufer et al. |
| 5,234,809 A | 8/1993 | Boom et al. |
| 5,565,318 A | 10/1996 | Walker et al. |
| 5,593,824 A | 1/1997 | Treml et al. |
| 5,763,157 A | 6/1998 | Treml et al. |
| 5,861,251 A | 1/1999 | Park et al. |
| 5,955,448 A | 9/1999 | Colaco et al. |
| 6,071,428 A | 6/2000 | Franks et al. |
| 6,127,155 A | 10/2000 | Gelfand et al. |
| 6,153,412 A | 11/2000 | Park et al. |
| 6,294,365 B1 | 9/2001 | De Rosier et al. |
| 7,544,506 B2 | 6/2009 | Breidford et al. |
| 7,618,777 B2 | 11/2009 | Myerson et al. |
| 7,763,453 B2 | 7/2010 | Clemmens et al. |
| 7,919,294 B2 | 4/2011 | Franco De Sarabia Rosado et al. |
| 8,835,146 B2 | 9/2014 | Battrell et al. |
| 2002/0173016 A1 | 11/2002 | Wurst et al. |
| 2003/0017567 A1 | 1/2003 | Parthasarathy et al. |
| 2003/0119042 A1 | 6/2003 | Franco De Sarabia Rosado et al. |
| 2003/0152994 A1 | 8/2003 | Woudenberg et al. |
| 2004/0045287 A1 | 3/2004 | Wylin |
| 2004/0241042 A1 | 12/2004 | Pugia et al. |
| 2005/0142563 A1 | 6/2005 | Haddad et al. |
| 2005/0142571 A1 | 6/2005 | Parthasarathy et al. |
| 2007/0003444 A1 | 1/2007 | Howell et al. |
| 2008/0064071 A1 | 3/2008 | Hogrefe et al. |
| 2009/0148933 A1 | 6/2009 | Battrell et al. |
| 2012/0156750 A1 | 6/2012 | Battrell et al. |

FOREIGN PATENT DOCUMENTS

| | | |
|---|---|---|
| EP | 1803825 A1 | 7/2007 |
| GB | 2009198 A | 10/1978 |
| VU | 2008/155524 A1 | 12/2008 |
| WO | 91/18091 A1 | 11/1991 |
| WO | 96/33744 A2 | 10/1996 |
| WO | 2005/118849 A1 | 12/2005 |
| WO | 2006/042838 A1 | 4/2006 |
| WO | 2007/106579 A2 | 9/2007 |
| WO | 2007/137291 A1 | 11/2007 |
| WO | 2008/036544 A1 | 3/2008 |
| WO | 2008/147382 A1 | 12/2008 |

OTHER PUBLICATIONS

Application and Declaration of U.S. Appl. No. 10/292,848, mailroom date Nov. 21, 2002, 53 Pages.
"NewProducts—Epicentre Biotechnologies—Long DNA kits" *Science* 314:323, Oct. 13, 2006.
Colaço et al., "Extraordinary stability of enzymes dried in trehalose: simplified molecular biology," *Bio/Technology* 10:1007-11, Sep. 1992.
Crowe et al., "Preservation of Membranes in Anhydrobiotic Organisms: The Role of Trehalose," *Science* 223:701-3, 1984.
Crowe et al., "The role of vitrification in anhydrobiosis," *Ann. Rev. Physiol.* 60:73-103, 1998.
Dorfman et al., "Contamination-Free Continuous Flow Microfluidic Polymerase Chain Reaction for Quantitative and Clinical Applications," *Anal. Chem.* 77(11):3700-4, Jun. 1, 2005.

(Continued)

*Primary Examiner* — Robert J Yamasaki
(74) *Attorney, Agent, or Firm* — Seed IP Law Group LLP

(57) ABSTRACT

Manufacturing methods and compositions are described for production of self-contained microfluidic cartridge devices with on-board reagents for molecular biological testing. Sensitive reagents are stored in dry form without lyophilization or freezing, and reconstituted at the point of use with either a biological sample or a sample eluate at the point of use. Manufacturing methods include sheet and roll fabrication processes where the reagents are printed in place and sealed within individual microfluidic cartridges before gel vitrification.

22 Claims, 12 Drawing Sheets

(56) References Cited

OTHER PUBLICATIONS

Franks, "Long-Term Stabilization of Biologicals," *Bio/Technology* 12:253-6, Mar. 1994.
Gibbs et al., "Nature of the Glass Transition and the Glassy State," *J. Chemical Physics* 28(3):373-393, Mar. 1958.
Green et al., "Phase Relations and Vitrification in Saccharide-Water Solutions and the Trehalose Anomaly," *J. Phys. Chem.* 93(8):2880-2, 1989.
Kajiwara et al., "Crystalline and amorphous phases in the binary system water-raffinose," *J. Chem. Soc. Faraday Trans* 93(9):1779-83, 1997.
Lukhtanov et al., "Novel DNA probes with low background and high hybridization-triggered fluorescence," *Nucl. Acids Res.* 35(5):e30, Jan. 26, 2007.
Marenco et al., "Fluorescent-Based Genetic Analysis for a Microfluidics Device," *Defence R&D Canada Contract Report*, Contract No. W7702-00-R849/001/EDM, Mar. 2004, 170 Pages.
Mollmann et al., "The Stablility of Insulin in Solid Formulations Containing Melezitose and Starch," *Drug Dev. Indust. Pharmacy* 32:765-78, 2006.
Ramachandran et al., "Dry-reagent storage for disposable lab-on-a-card diagnosis of enteric pathogens," *Proceedings of the 1st Distributed Diagnosis and Home Healthcare (D2H2) Conference*, Arlington, Virginia, Apr. 2-4, 2006, 4 pages.
Ramanujam et al., "Ambient-Temperature-Stable Molecular Biology Reagents," *BioTechniques* 14(3):470-474, 1993.
Schebor et al., "Glassy State and Thermal Inactivation of Invertase and Lactase in Dried Amorphous Matrices," *Biotechnol Prog.* 13(6):857-63, 1997.
Slade et al., "Non-equilibrium behavior of small carbohydrate-water systems," *Pure & Appl. Chem.* 60(12):1841-64, 1988.
Wikipedia, "Injection molding"[Online] Oct. 17, 2007, XP002602263, URL=http://web.archive.org/web/20071019005409/http://en.wikipedia.org/wiki/Injection_molding> [retrieved on Sep. 23, 2010], p. 3, paragraph 3.
Wolanczyk, "Differential Scanning Calorimetry Analysis of Glass Transitions," *Cryo-Letters* 10:73-76, 1989.
Zhang et al., "Development of Continuous_flow PCR Chip Corresponding Technologies," *Journal of Instrumental Analysis* 23(6):114-118, 2004. (translation of abstract only).
Zhang et al., "Miniaturized PCR chips for nucleic acid amplification and analysis: latest advances and future trends," *Nucl. Acids Res.* 35(13):4223-37, Jun. 18, 2007.
Weigl et al., "Fully integrated multiplexed lab-on-a-card assay for enteric pathogens," *Proc. of SPIE* 6112:611202-1-611202-11, 2006.

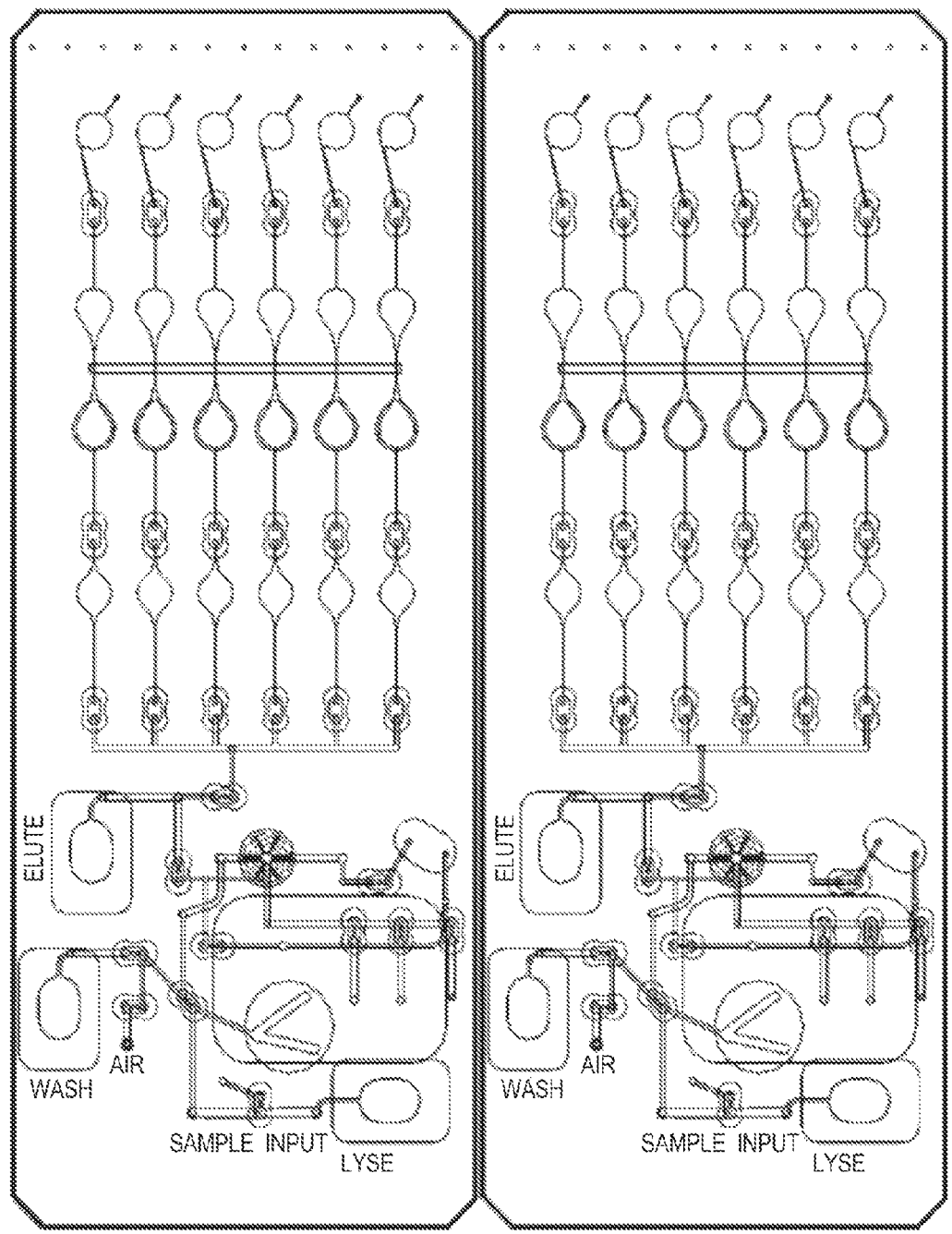
FIG_1A

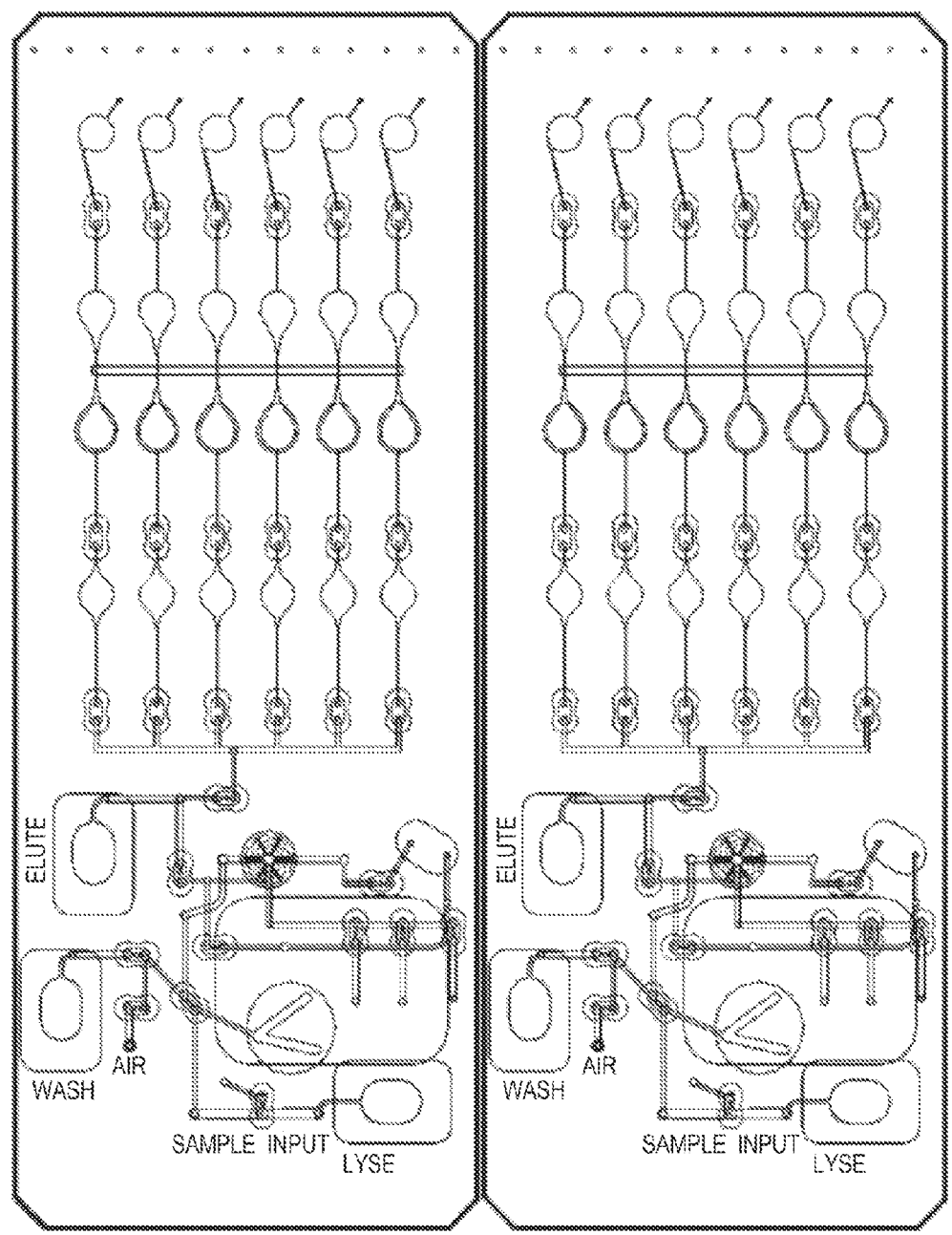
FIG_1B

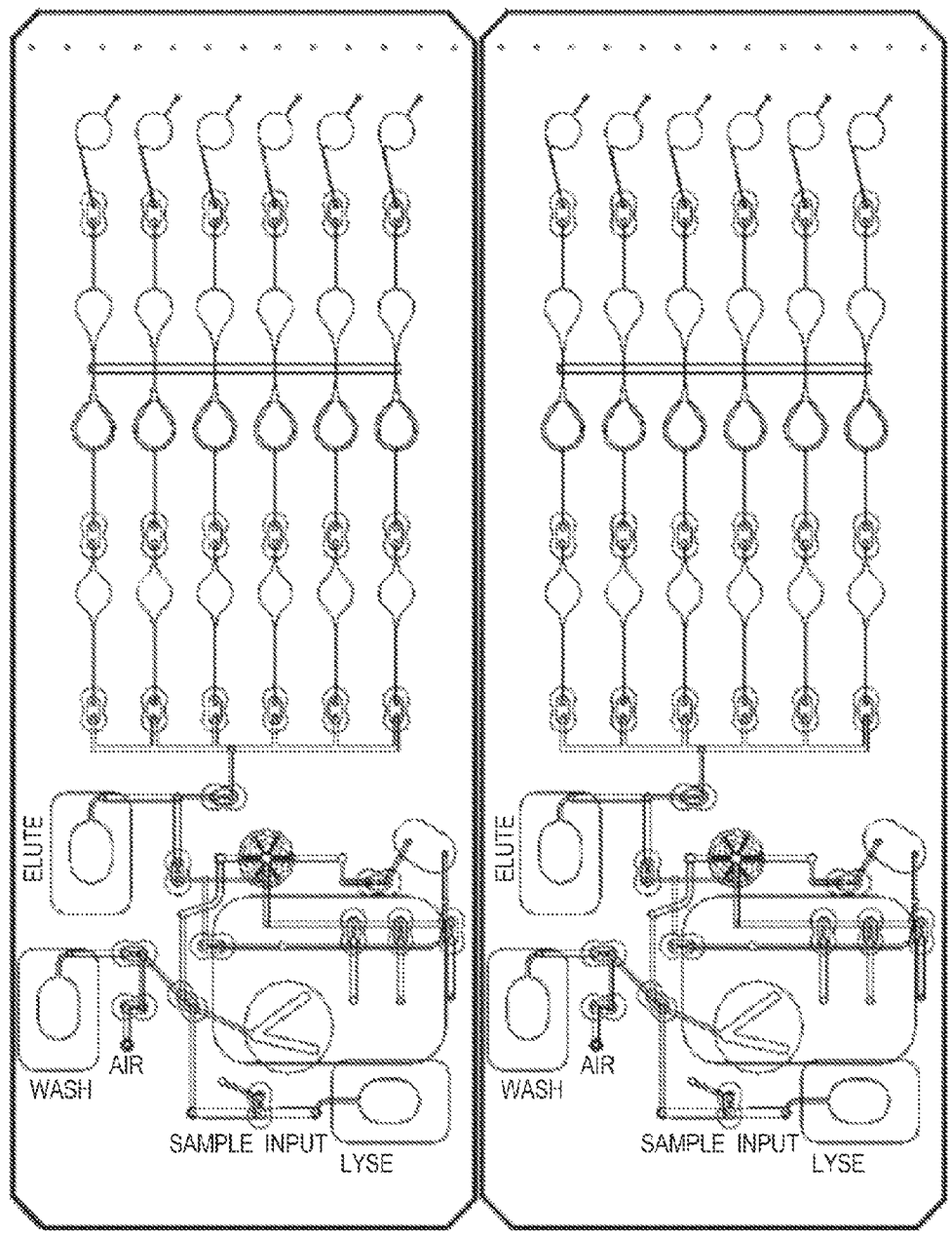
FIG_1C

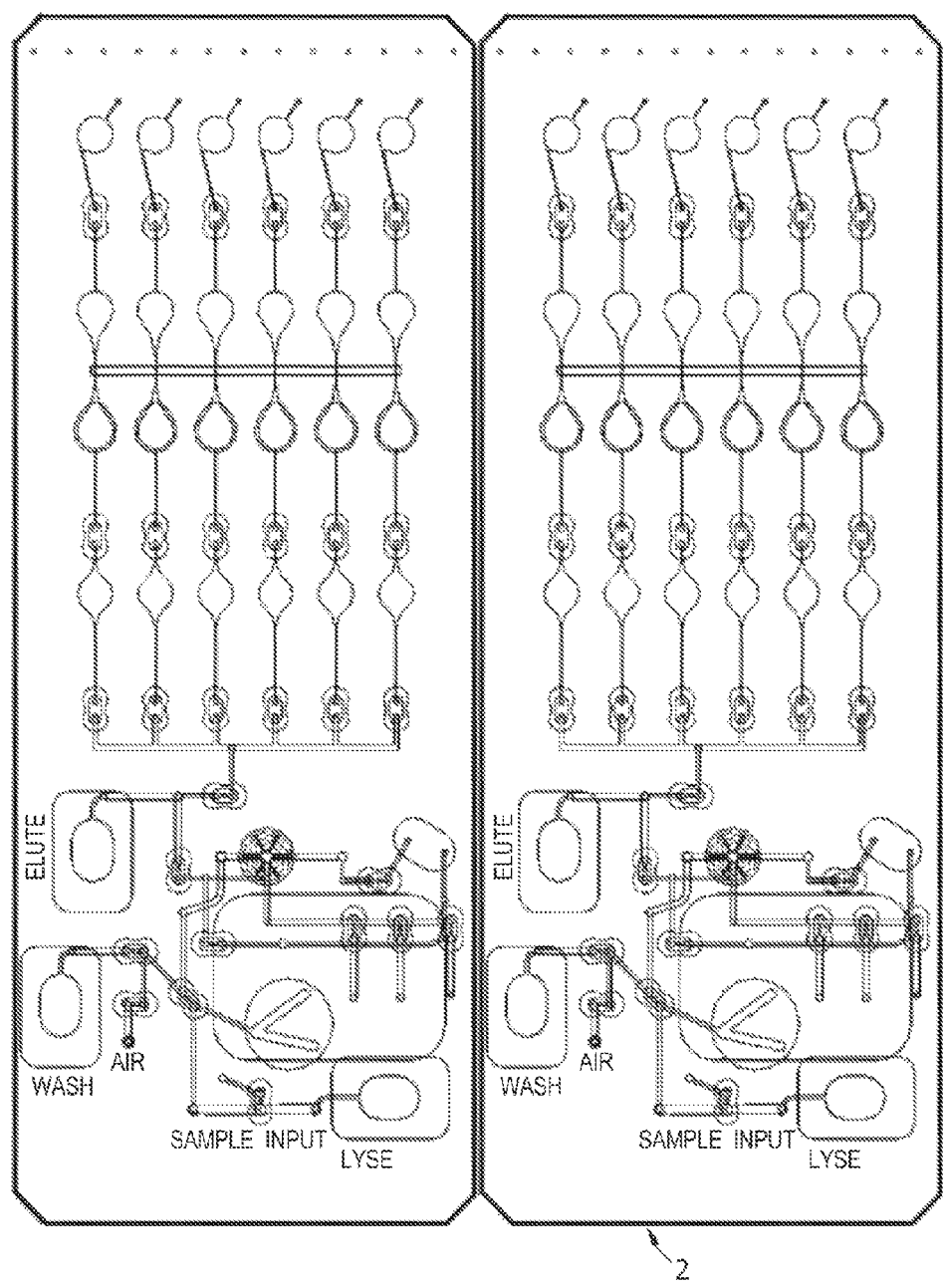
FIG_1D

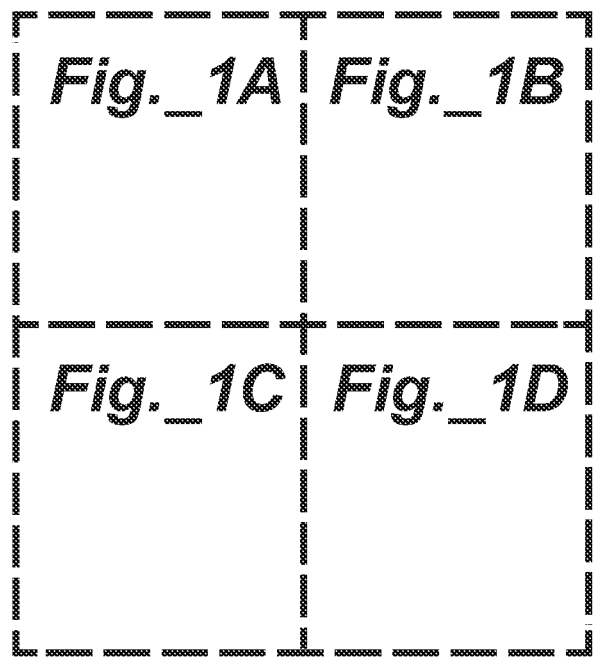
FIG_1E

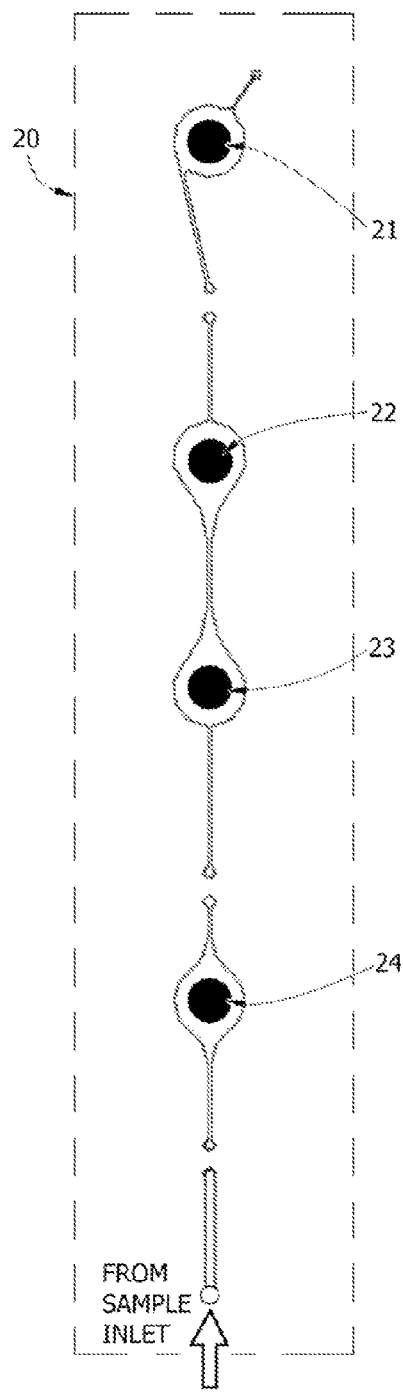
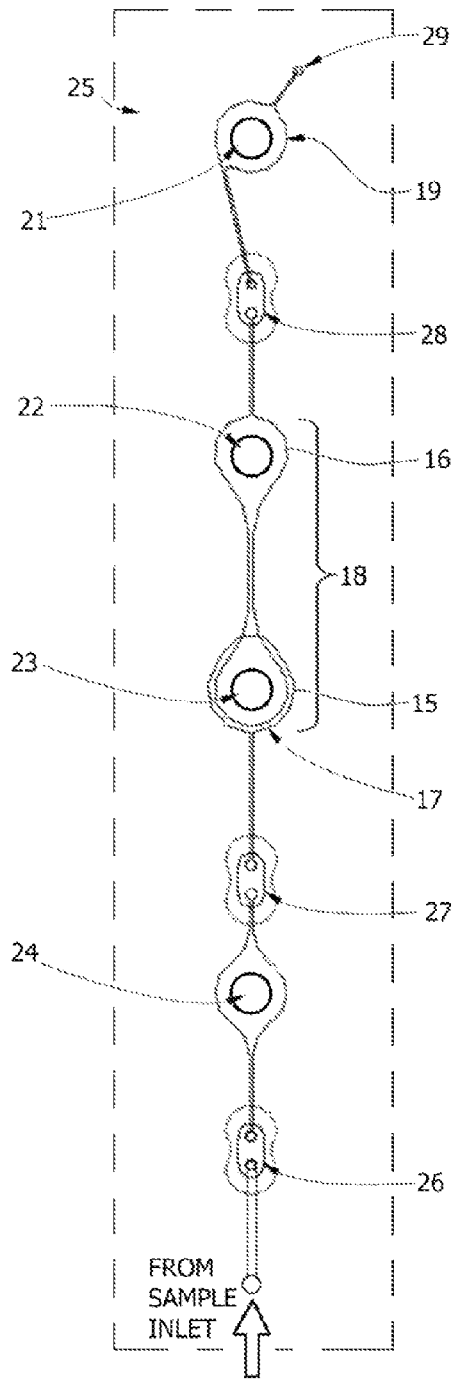
FIG. 2A
FIG. 2B

COMPOSITIONS AND METHODS FOR DEHYDRATED STORAGE OF ON-BOARD REAGENTS IN MICROFLUIDIC DEVICES

CROSS-REFERENCE TO RELATED APPLICATION

This application is a divisional of U.S. patent application Ser. No. 13/323,684, filed Dec. 12, 2011, (now U.S. Pat. No. 8,921,085), which is a continuation of International PCT Patent Application No. PCT/US2010/038141, which was filed on Jun. 10, 2010, which claims the benefit under 35 U.S.C. § 119(e) of U.S. Provisional Patent Application No. 61/186,442, filed Jun. 12, 2009, which applications are incorporated herein by reference in their entireties.

BACKGROUND

Field

The invention relates generally to the field of molecular diagnostic assays in microfluidic cartridges having on-board dehydrated reagents, where the reagents are stabilized by dehydration without lyophilization, and to methods of manufacture of microfluidic cartridges having same.

Description of the Related Art

Microfluidic cartridges are well suited for diagnostic molecular biology due to their convenience, operability by unskilled workers, and ready disposability. Each cartridge contains all reagents for a particular assay, so that only sample need be added. The cartridge is then simply inserted into an automated apparatus for performing the assay. However, since first conceived in the early 1990's, the road to development of these cartridges has taken two decades and obstacles to commercialization continue. Shelf-life of the cartridges is a particular concern, because most intended users lack access to frozen storage facilities.

While "freeze drying" has been successfully employed for extended storage of moisture-sensitive reagents at room temperature, the manufacturing of microfluidic cartridges does not readily permit use of freeze drying as part of the process. Additional assembly is required after the reagents are placed within wells or channels of the partially assembled device. Powders or loose spheres can become dislodged or fail to seat in the correct positions, and interfere with high speed assembly of cartridges formed from sheets or rolls. Dry reagents can also interfere with the use of adhesives. The final assembly of a microfluidic cartridge involves procedures for demasking, lamination, gluing and/or ultrasonic welding not readily compatible with freeze-drying technology on a commercial scale. Also, the moist or hot environments encountered in the assembly of microfluidic cartridges can inactivate freeze-dried reagents even before the product is fully assembled.

Alternatively, dehydration in glass form is known to preserve the function of enzymes or reagents during storage above freezing, but the art is highly unpredictable, and methods and compositions must be varied for each reagent studied—with no particular expectation of success.

Protein reagents that may be required for assembly of a self-contained microfluidic cartridge for a molecular biological assay include: TAQ polymerase, DNA polymerase, RNA polymerase, reverse transcriptase, RNAase H, proteinase K, immunoglobulin, luciferase, pyrophosphatase, chromopeptidase, lysozyme, and so forth. Other reagents likely to have sensitivity to light, moisture or heat include nucleotide triphosphates, deoxynucleotide triphosphates, primers and probes.

PCR forms the basis of a large family of molecular biological assays, and is currently the gold standard for many molecular diagnostics not available in a microfluidic cartridge format. Adapting PCR to a microfluidic format will involve developing methods for stable on-board storage of reagents including TAQ polymerase, reverse transcriptase, deoxyribonucleotide triphosphates, primers and probes. The DNA polymerases of thermophilic organisms used in PCR, generically referred to as "TAQ polymerases" by virtue of their first discovery in *Thermus aquaticus*, have proven particularly difficult to stabilize for room temperature storage. Nonetheless, the development of PCR products with a commercially useful shelf life at room temperature in a microfluidic device depends on a solution to this problem.

TAQ has 5'-3' polymerase and exonuclease activity, but not the 3'-5' proofreading capacity of other polymerases. The enzyme structure, however, is shared with other DNA polymerases and contains an opposable thumb-palm domain split by a deep cleft associated with DNA template binding. Features associated with thermostability of TAQ polymerases include increased ratios of Arg to Lys, Glu to Asp, Ala to Gly, Thr to Ser, and an absence of cysteine. Folding at elevated temperature is established and maintained by hydrophobic, hydrogen bonding, electrostatic and van der Waal's interactions.

Enzymes are complex folded nanomachines, having cooperative motions and flexibility related to their catalytic function and folding. Certain structural sub-domains are relatively fixed in structure and others are more fluid and dynamic. Ideally, the native state is preserved during storage by dehydration, but dehydration most commonly results in some level of destabilization of folding. Denaturation and loss of activity results from enzyme unfolding; changes in structure following dehydration (or freezing) can be so severe that refolding into an active "native state" form does not occur following rehydration.

The role of water in enzyme structure is firmly established. The degree of hydration of a protein may be expressed by "Dh", where Dh≅0.4 (g $H_2O$/g protein) indicates a full hydration shell or monolayer of water surrounding the protein. Intermediate levels of hydration are also known. At Dh≅0.15-0.2 water is sufficient only to associate with more polar and ionic surfaces and enzymatic activity is lost. Most lyophilization processes result in Dh≅0.02. In the absence of the dielectric shielding of water, electrostatic interactions can result in denaturation. Water dominates protein structure by continuously breaking and reforming hydrogen bonds in the hydration shell (leading to both hydrophobic and hydrophilic interactions), as well as by guiding secondary and tertiary structure such as α-helix and β-turn motifs through inter-peptide and side chain interactions. The liquid crystalline, hydrogen bonding capacity of water as a solvent lubricates or "plasticizes" the motions of structural domains of the enzyme.

Amorphous solids are preferred for "dry" storage of reagents because rehydration proceeds more rapidly than for the corresponding crystalline state. Ideally, the protein is stabilized in a solid, non-hygroscopic, glassy matrix, which undergoes a controlled devitrification when rehydrated with excess water. The preferred state has much in common with the glassy state formed by supercooling a liquid. Similarly, protein domains can be frozen in an amorphous "glassy" or gel-like state at or below a temperature $T_d$ (dynamical transition temperature), which is analogous to the $T_g$ (glass transition temperature) for formation of a glassy state in small molecules and polymers. Below $T_d$, protein unfolding is effectively inhibited. Similarly, dehydration to a critical level can be associated with inhibition of protein unfolding: at Dh<0.2 the hydration shell is patchy, and there are insufficient water molecules to execute the hydrogen bond rearrangements associated with unfolding of protein domains, even though the thermal energy available at room temperature is sufficient to denature the protein.

Of particular interest is the dehydration of proteins within glasses composed of lyoprotectants, molecules that protect the protein from denaturation during dry storage. Activity of lyoprotectants is perhaps best explained by a "water replacement model" in which the lyoprotectant is thought to interact directly with the protein through hydrogen and hydrophobic bonding, somehow offsetting the denaturing effect of removal of water. Glycerol, for example is thought to substitute for water in the protein's hydration shell and to effectively plasticize the dehydrated protein in a rehydratable form, albeit without the conformational instability of water.

Thus a common framework may be used to consider the amorphous glassy state formed by cooling a protein in an intimate mixture with a glass-forming molecule and the amorphous glassy state formed by dehydration of that mixture. The solid product in both cases is composed of protein conformers having varying degrees of native state which are "solvated" and molecularly dispersed in an amorphous glass such as a sugar. Protein and sugar mixtures for example have been found calorimetrically to have a bulk $T_g$ intermediate between the $T_g$ of the sugar and the $T_d$ of the protein in proportion to the composition of the mixture. Similarly, the $T_d$ of a protein may be modulated by intimate association of the protein with a suitable lyoprotectant, although the mechanism is not fully understood. Thus the conformation of the dewatered protein is believed to be somehow coupled to the molecular structure of the glass.

Candidate lyoprotectants include polyhydroxy compounds (PHCs) generally, particularly a variety of sugars (including monosaccharides, disaccharides, trisaccharides, and oligosaccharides), sugar alcohols, and a variety of polyhydoxy small molecules and polymers. Lactitol, mannitol, maltitol, xylitol, erythritol, myoinositol, threitol, sorbitol (glucitol), and glycerol are examples of sugar alcohols. Non-reducing sugars include sucrose, trehalose, sorbose, stachyose, gentianose, melezitose and raffinose. Derivatives of sugars that are lyoprotectants include methylglucoside and 2'-deoxyglucose, among others. Sugar acids include L-gluconate and metallic salts thereof. Less preferred for most applications include reducing sugars such as fructose, apiose, mannose, maltose, isomaltulose, lactose, lactulose, arabinose, xylose, lyxose, digitoxose, fucose, quercitol, allose, altrose, primeverose, ribose, rhamnose, galactose, glyceraldehyde, allose, apiose, altrose, tagatose, turanose, sophorose, maltotriose, manninotriose, rutinose, scillabiose, cellobiose, gentiobiose, and glucose. Also useful are polyvinylpyrrolidones, polyacrylamide, polyethylimine, pectin, cellulose, derivatized celluloses such as hydroxymethylcellulose, hydroxyethylcellulose, and hydroxypropylmethylcellulose, hydroxyethylstarch, soluble starches, dextrans, highly branched, high-mass, hydrophilic polysaccharides such as Ficoll®. Glass-forming albumins, gelatins and amino acids have also found use. By trial and error, useful mixtures of the above have also been discovered, typically differing for each target protein.

Success in formation of a glass is also known to be sensitive to rate of cooling, concentration, pressure and other process parameters such as the presence or absence of seed crystals. It must be recalled that a glass is a metastable state. The difficulties of these complex systems are illustrated by the following example, taken from WO 1996/033744, where it was reported that an amorphous solid freeze-dried composition of calcitonin 2% in lactose 95% with 2% residual water was raised above its $T_g$ of 40° C., resulting in irruptive crystallization of the lactose and formation of a water of crystallization composed of 60% water and 40% protein, which was excluded from the crystalline phase. The glass temperature of the solution phase was below freezing and as a result the protein then very rapidly lost biological activity at room temperature. Similar inactivation of enzymes has been noted with crystallized sucrose (Schebor C et al, 2008, Glassy state and thermal inactivation of invertase and lactase in dried amorphous matrices. Biotech Progress 13:857-863).

Rosen, as disclosed in expired U.S. Pat. No. 4,891,319, discovered that trehalose, which has a higher $T_g$ than lactose or sucrose, is lyoprotective when proteins are dried at room temperature, avoiding the rigorous conditions of freeze drying and spray drying, and reported that fluorescence markers may also be dehydrated in this way. Rosen suggested sugar:protein ratios of 1.4:1 to 10:1. Trehalose was proposed to act as a dry scaffold maintaining the structural integrity of the macromolecule when water was removed. These findings were further extending elsewhere (Colaco C et al, 1992, Extraordinary stability of enzymes dried in trehalose: simplified molecular biology, Bio/Technology 10:1007-11) and in U.S. Pat. No. 5,955,448 it was reported that various carbohydrates, including lactose or sucrose, may be employed as long as the formulation also includes an inhibitor of the Maillard browning reaction. Related observations have been reported by Franks (U.S. Pat. No. 5,098,893) and by Wettlaufer (U.S. Pat. No. 5,200,399), with comments on the importance of oxygen, light and chemical reactions in loss of activity of vitrified biological substances.

Sucrose, sorbitol, melezitose and raffinose have also been suggested as preferred lyoprotectants. However, to our knowledge, no success has been reported in stabilizing, without lyophilization, dry TAQ for extended storage stability periods with trehalose or any other sugar. To the contrary, in the declaration of A Madejón (FIG. 5—source: file wrapper of U.S. patent application Ser. No. 10/292,848), it is shown that trehalose is at most partially protective in dry reagent forms stored at 4° C. for 1 week, and that the standard PCR mixture without a lyoprotectant has more residual activity at 37° C. after one week than the dry reagent with the lyoprotectant. Madejón further shows that melezitose of itself is not protective at all. Referring to the gel, which is reproduced here as FIG. 5, lanes 1-9 (between the ladders) were run after reactant storage at 4° C.; lanes 10-18 after storage at 37° C. ("M"-melezitose, "L"-lysine, "G"-glycogen, "T"-trehalose, "S"-standard mix with no lyoprotectant).

Trehalose has been reported as unusual or even extraordinary in that addition of small amounts of water does not depress $T_g$, as in other sugars (Crowe J H et al, 1998, The role of vitrification in anhydrobiosis. Ann Rev Physiol 60:73-103). Instead, a dihydrate crystal of trehalose forms, thereby shielding the remaining glassy trehalose from effects of the added water. Franks, however, in U.S. Pat. No. 6,071,428 shows that this effect is not remarkable, and that raffinose pentahydrate is also useful in storing enzymes in a dry state. The crystalline pentahydrate is reported to coexist with a surrounding glassy state of anhydrous material. These hydrated saccharides are not generally associated with formation of waters of crystallization or irruptive crystallization which would favor denaturation.

Arieli, in WO 2007/137291, proposes stabilization of TAQ with stabilizing agents such as sucrose, trehalose, melezitose, sugar alcohols, and reducing sugars in combination with BSA by drying above freezing, typically by drying at 55° C. for 1-3 hrs. Qualitative data illustrated in the application demonstrate activity of TAQ after overnight or short term storage. However, no indication is given as to the degree of hydration (Dh) achieved in the drying process, and as is already known, TAQ retains full activity overnight in aqueous solution at room temperature (FIG. 6—source: Marenco A et al, 2004, Fluorescent-based genetic analysis for a microfluidics device, Defence R&D Canada Contract W7702-00-R849/001/EDM Final Report), and presumably for short term storage as well. Thus it is unclear whether the dehydration and glassy state achieved was sufficient for long term storage over months or years. Rosado (US Pat. Appl. 2003/0119042) has argued that TAQ is best stabilized in a fully hydrated "gelified" form, however the data disclosed suggests that only limited duration of stability was achieved, perhaps a few days or weeks.

Development of frozen commercial formulations of TAQ have been reported in U.S. Pat. No. 6,127,155, for example. However, frozen storage requires special equipment typically not available at point-of-care facilities where microfluidic cards find usage. Also of note, a number of investigators have reported success lyophilizing TAQ preparations. These include Walker (U.S. Pat. No. 5,565,318), Treml (U.S. Pat. No. 5,763,157), and Park et al. (U.S. Pat. Nos. 5,861,251 and 6,153,412). Park describes lyophilization of TAQ in the presence of glucose, sorbitol, sucrose or Ficoll®. Klatser P R et al describe a lyophilized PCR Mix using trehalose as cryoprotectant and Triton X-100. Klatser found TAQ activity of their lyophilized mixture when rehydrated at up to 1 year post preparation. Commercially available lyophilized beads containing TAQ with excipients are also available (Ready-to-Go PCR beads, Amersham Biosciences; Sprint™ Advantage®, Clontech, Mt View Calif.). Once lyophilized, the products are hygroscopic and sensitive to humidity and must be immediately sealed. The products apparently must also be held on ice during the rehydration process with ultra-pure water and subsequently prior to use, rendering their use in next-generation reagents-on-board microfluidic devices difficult if not impossible.

In contrast, next-generation microfluidic devices are configured so that use of ice or pure water during rehydration of reagents is not possible. The device reagents are typically rehydrated by sample or by an eluate prepared from the sample, for example by the method of Boom (U.S. Pat. No. 5,234,809). Thus, there is still a need in the art for a method of achieving ambient stabilization of DNA polymerase in the context of a PCR reagent mix that does not involve lyophilization and retains sufficient reliability over an extended storage time sufficient for practical commercialization of sensitive diagnostic assays in a microfluidic card.

Thus the disclosures to date do not apparently enable a formulation suitable for extended stable dry storage of TAQ polymerase without lyophilization or freezing. As commercialization of microfluidic devices for diagnostic applications moves closer to fruition, a workable solution to this problem is more urgently needed.

BRIEF SUMMARY

Room temperature dry storage of molecular biological reagents for nucleic acid assays, particularly TAQ polymerase, on microfluidic cards has proven difficult. As demonstrated here, reagents are printed in liquid form in a matrix containing lyoprotectants. Automated printing devices print microliter droplets of the matrix with biologicals in the microfluidic channels of the card without a freezing or lyophilization step which would disrupt the fabrication of the card device. After the droplet matrix has gelled, typically by drying at controlled room temperature for about 10 minutes, the assembly of the cartridge is then completed. Happily, storage stability periods of six months or more are achieved by this process, sufficient for commercialization.

With reference to TAQ polymerase, we reasoned that an enzyme adapted for activity in a high temperature environment is likely to have a high $T_d$, as evidenced by a $V_{max}$ for many TAQ polymerases around 75° C., and to best preserve that native state, should be coupled in the vitrified state with a glass having a relatively high $T_g$. We also recognized that other excipients such as surfactants may be needed to stabilize the highly folded structure of TAQ during dry storage, particularly in microfluidic devices, because the reagent material is preferably printed on a low surface activity surface such as polyethylene terephthalate (PET) and is subjected to interfacial adsorption and denaturation during drying and rehydration. Passivation methods were also adopted. Once reagents are printed in place, the microfluidic devices are then further processed by lamination or ultrasonic welding to form the completed cartridge body. Use of automated printers for dispensing reagents followed by gel vitrification permits roll-to-roll and sheet-by-sheet manufacture, processes that are not compatible with a lyophilization step due to the technical difficulties of freezing and vacuum processing a compound plastic sheet or roll containing sealed reagents.

Following a period of drying at controlled room temperature, the method relies on the use of a gel dessicant in sealed moisture-proof bags to complete the vitrification of the enzyme inside the cartridge body. A sample inlet port and waste vent provide the openings in the cartridge body through which the slow process of dehydration below Dh<0.2 continues. The enzyme thus passes through a partially hydrated state over a period of a few weeks during dehydration. While not bound by theory, we believe that the extended progressive time-dehydration curve is essential for the enzyme to stabilize in native state during the gradual substitution of a sugar or other polyol for water as hydrogen-bond donor. Surprisingly, we find that TAQ activity actually increases sharply during this drying process. While not bound by any particular theory, we explain this as recovery of latent activity of conformers in the frozen stock through a process of refolding in the partially hydrated state, which more closely resembles an intracellular cytosol in osmolarity. The material progresses from a gel to a composite gel-like glass during this process, developing a composite $T_g$ (ie. resulting from more than one glass-precuror in the mixture) that is in excess of room temperature by virtue of the high $T_g$ of the sugar.

It was found that co-lyoprotectants, including high molecular weight polyethylene glycol (PEG), cellulose gums, albumin or gelatin, enhancers, amino acids and optionally selected fluorosurfactants are useful in this process and contribute to the composite $T_g$. While not bound by theory, it is thought that co-lyoprotectants may selectively associate with the protein shell while not disrupting the bulk gel glass formed by the sugar. The method described is optimized for TAQ polymerase, but can be adapted if necessary and is effective in stabilizing other biological reagents such as dNTPs, DNA polymerases in general, RNA polymerases in general, reverse transcriptase, proteinase K, RNAase H, primers and probes as required, without incompatibility with a roll-to-roll or sheet-by-sheet process of producing the microfluidic cartridges.

Advantageously, lyophilization and frozen storage conditions are not required. While not limited thereto, the general method finds broad use in manufacture of microfluidic devices and kits for diagnostic nucleic acid assays. Thankfully, microfluidic cartridges mass produced according to these methods have a storage shelf life of greater than 6 months.

BRIEF DESCRIPTION OF THE DRAWINGS

The teachings of the invention can be better understood by considering the following detailed description in conjunction with the accompanying drawings and claims, in which:

FIGS. 1A-1E show a sheet of detachable microfluidic cartridges for a nucleic acid assay. The sheet is an intermediate in the manufacturing of individual microfluidic cartridges. The sheet in this case contains 8 detachable microfluidic cartridges.

FIGS. 2A and 2B illustrate schematically the printing of reagent spots on a microfluidic cartridge during final assembly. FIG. 2A shows an underlayer with four liquid reagent spots (black circles); FIG. 2B shows the completed cartridge assembly with enclosed gel spots (open circles).

DETAILED DESCRIPTION

Figure 3A:
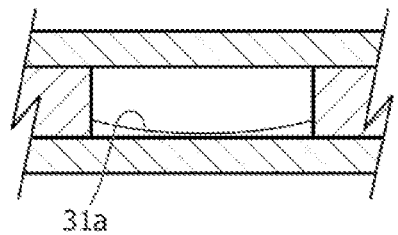
FIGS. 3A-3D illustrate several configurations in which a liquid reagents may be applied in a microfluidic channel or chamber; the liquid reagent gels in place prior to final assembly.
Figure 3B:
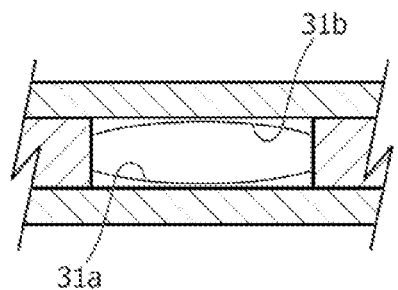
Figure 3C:
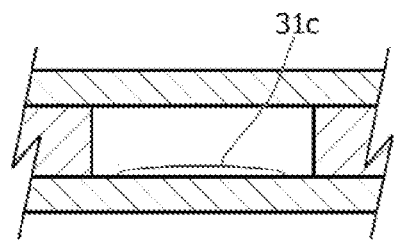
Figure 3D:
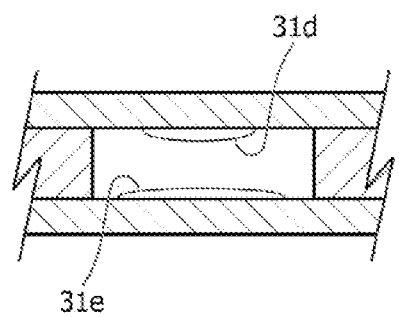

Certain meanings are defined here as intended by the inventors, ie. they are intrinsic meanings. Other words and phrases used here take their meaning as consistent with usage as would be apparent to one skilled in the relevant arts. When cited works are incorporated by reference, any meaning or definition of a word in the reference that conflicts with or narrows the meaning as used here shall be considered idiosyncratic to said reference and shall not supercede the meaning of the word as used in the disclosure herein.
Definitions Lyoprotectant: a molecule that protects a protein, primer or probe, for example a TAQ polymerase, from denaturation and loss of biological activity during dry storage. Many lyoprotectants are polyols, but the class may also include amino acids, peptides, proteins, as well as PHCs, sugars, polyvinylpyrrolidinones, PEGs, and the like. It should be understood that the definition also includes co-lyoprotectants, where a first substance and a second substance having a synergic protective effect with the first are used in a mixture.

"$T_g$" is a glass transition temperature, the temperature above which the viscosity of an amorphous glassy material drops rapidly, progressing from a gel to a deformable plastic to a liquid, and conversely the temperature below which an amorphous non-crystalline solid forms. It has been thought that a $T_g$ of 40° C. or greater will ensure stability of a reagent at room temperature but this is unknown for TAQ polymerases. Generally $T_g$ is determined using differential scanning calorimetry (DSC) and can be defined as the onset, midpoint or endpoint of the transition. Technical details are provided in "Differential Scanning calorimetry Analysis of Glass Transitions" by Jan P. Wolanczyk, 1989, Cryo-Letters, 10, 73-76 (1989) and Gibbs J H and E A DiMarzio, 1958, Nature of the Glass Transition and the Glassy State, J Chemical Physics 28:373-393. Glasses of value in the method are generally not formed from a pure glass precursor, but are instead formed from a lyoprotectant and a co-lyoprotectant, co-solvent, co-surfactant or added excipient as a mixture, and are thus termed "composite glasses". These composite glasses may have intermediate glass and "gel-like" properties and have hydration values ranging from about 0.01≤Dh≤0.4, more preferably 0.022≤Dh≤0.2. The $T_g$ of composite materials is generally dependent on the $T_g$ values of the individual constituents (Franks, F, 1994, Long term stabilization of biologicals, Bio/Technology 12:253-56). A preferred $T_g$ is greater than 20 degrees above the intended temperature of storage.

Probe: A "probe" is a nucleic acid capable of binding to a target nucleic acid by complementary base paring with sufficient complementarity to form a stable double 5 helix at room temperature. Probes may be labeled. Suitable labels that can be attached to probes include, but not limited to, radioisotopes, fluorophores, chromophores, mass labels, electron dense particles, magnetic particles, spin labels, molecules that emit chemiluminescence, electrochemically active molecules, enzymes, cofactors, and enzyme substrates. Fluorescent probes include intercalating probes, such as Syber Green® (Molecular Probes), ethidium bromide, or thiazole orange, FRET probes, TaqMan® probes (Roche Molecular Systems), molecular beacon probes, Black Hole Quencher™ (Biosearch Technologies), MGB-Eclipse® probes (Nanogen), Scorpions™ (DxS Ltd) probes, LUX™ primer-probes (Invitrogen), Sunrise™ probes (Oncor), MGB-Pleiades (Nanogen), and so forth. Recent advances in probe technologies are reviewed by Lukhtanov E A et al, 2007, Novel DNA probes with low background and high hybridization-triggered fluorescence, Nucl Acids Res 35:e30, for example.

"Storage stability period" refers to a period of time, e.g. "shelf life", where a dry reagent mixture is stored in a microfluidic card under controlled conditions while retaining biological activity. A TAQ polymerase "retains its biological activity" in a reagent composition, if the biological activity of the biologically active material is efficacious at any given time in performing a PCR amplification. A preferred composition has a shelf life of greater than 6 months.

Microfluidic cartridge: a "device", "card", or "chip" with internal fluid-handling mesostructures by convention having at least one dimension less than 500 um. These fluidic structures may include microfluidic channels, chambers, valves, vents, vias, pumps, inlets, nipples, and detection means, for example.

Microfluidic channels are enclosed conduits or passages for a fluid having a z-dimension (height or depth) of less than 500 um, more preferably about or less than 150 um (about 4 mils), and a cross-sectional area that is generally broader than deep. The most narrow dimension of a channel has the most profound effect on flow, Reynolds Number, pressure drop, and in the devices described here, the most narrow dimension is typically the z-dimension or diameter. When formed by injection molding, the channel roof and walls are typically joined by a radius. Some microfluidic channels have a circular cross-section and are characterized by a diameter. Other shapes are also possible.

It will be recognized that the words "top", "bottom", "upper", "lower", "side", "roof", "floor", and "base" as used here are relative terms and do not necessarily describe the orientation of the device or device components in relation to the plane of the earth's surface unless explicitly stated to be so. The preferred use of the devices flat on the surface of a table is not intended to be limiting and the z-axis is generally chosen to be perpendicular to the major plane of the device body only as a matter of convenience in explanation and manufacture.

"Conventional" is a term designating that which is known in the prior art to which this invention relates.

"About" and "generally" are broadening expressions of inexactitude, describing a condition of being "more or less", "approximately", or "almost" in the sense of "just about", where variation would be insignificant, obvious, or of equivalent utility or function, and further indicating the existence of obvious minor exceptions to a norm, rule or limit.

Unless the context requires otherwise, throughout the specification and claims which follow, the word "comprise" and variations thereof, such as, "comprises" and "comprising" are to be construed in an open, inclusive sense, that is as "including, but not limited to".

Engineering and Handling of Microfluidic Devices for PCR

PCR in a microfluidic device is challenging due to the high surface area to volume ratio typical of the devices. Reaction volumes of a few microliters of sample are typical, and channel and chamber dimensions are typically smaller than 500 micrometers in width and perhaps 10 to 20% of that in depth. The microfluidic devices of the invention are small chemical reactors, preferredly mass produced from a plastic, having miniature channels and chambers containing pre-printed assay reagents.

In a preferred embodiment, all reagents required for performing a diagnostic assay are pre-positioned within the device so that the device is a self-contained disposable apparatus for performing a nucleic acid diagnostic assay. Optionally, the device also contains on-board diluents, wash solutions, and a waste trap of volume sufficient to contain all liquid wastes generated in the assay.

Details of the design and features of microfluidic cards suitable for practice of the present invention are disclosed for example in U.S. patent application Ser. No. 12/207,627, "Integrated Nucleic Acid Assays"; Ser. No. 11/562,611 "Microfluidic Mixing and Analytical Apparatus"; Ser. No. 12/203,715 "System and Method for Diagnosis of Infectious Diseases"; and Ser. No. 10/862,826 "System and Method for Heating, Cooling and Heat Cycling on Microfluidic Device", all co-assigned to the Applicant. The arts are the subject of a recent review by Zhang (2007, Miniaturized PCR chips for nucleic acid amplification and analysis: latest advances and future trends. Nucl Acids Res 35:4223-37).

As known in the art, microfluidic PCR may be performed in four configurations of PCR thermocycling reactors: a) serpentine, b) circular, c) reciprocating, and d) single chamber with localized heating and cooling. Serpentine reactors contain extended channels looping back and forth between two or three temperature zones, circular reactors are single loops crossing two or three temperature zones, reciprocating reactors contain two or three chambers at different temperatures, each chamber interconnected for exchange of the reaction mixture, and single chamber-based contain the reaction mixture with provision for localized heating and cooling, such as by Peltier thermoelectronics. Serpentine, circular and reciprocating reactors all require a pump or pumps to circulate the reaction mixture through or between temperature zones. Architecture of the microfluidic devices is varied to reflect these configurations.

Assays may include end-point or kinetic (also termed "real time") detection. Where an indicator reagent such as a probe is used, it may be added during the amplification or after the amplification. Preferred are fluorescent, fluorescence quenching, and "up-converting" fluorescent probes as are known in the art.

In a preferred embodiment, a biological sample containing a nucleic acid is pipetted into a port in a microfluidic card, which is then sealed for the remainder of the assay. A pneumatic controller is used to direct the sample and liquid reagents as required to complete the assay. In a first step, the nucleic acid of the sample is optionally extracted on a solid phase matrix and rehydrated in a PCR buffer before being contacted with a dried PCR reagent containing primers. A dry reagent containing TAQ polymerase is provided separately. Thermocycling is then performed on card and positive detection of amplicon is made by a variety of methods, including use of fluorescent probes that are supplied on the microfluidic device.

Because of the interfacial tension between water and plastics, surfactants and co-surfactants such as PEG or albumin are sometimes used to reduce adsorption of biologicals to the plastic surfaces of the microfluidic device. Surface active agents known of value in reducing adsorptive losses include Tween-20, Triton X-100, Nonidet P40, PEG-8000 and bovine serum albumin. These substances also are thought to reduce aggregation of TAQ polymerase and are frequently used to increase polymerase activity. Also useful in our hands have been techniques for passivating the plastic surfaces where contacted biologicals. These techniques involve passive and covalent modification of the plastic with hydrophilic molecules such as polyethylene glycol diacrylate, where the plastic is activated with a free radical initiator. Surfaces not to be modified, such as those which will be glued together, are masked during the passivation treatment.

In general, dNTPs, magnesium salt, potassium chloride, sodium chloride, buffers, probe species, optionally primers, and non-specific wetting agents or surfactants are optionally combined in a "master-mix" that is aliquoted and dried on-board the microfluidic device.

Experience has shown that primers are best printed separately and at a distance from the TAQ polymerase reagent. Reasons for this are not fully understood but yields in our hands were consistently enhanced with this modification. Primers store well in the dry state and may be stabilized for extended room temperature storage by gel-to-glass vitrification from solutions in 1.6% trehalose in water in the presence of dessicant in a sealed pouch, for example.

During manufacture of a microfluidic device with on-board reagents, solutions containing glasses, excipients, and biological reagents are typically printed in the channels or chambers of the microfluidic devices using a variety of automated droplet dispenser equipment. A cover layer or lid is then applied to the device and the device is sealed. After assembly and inspection, the completed microfluidic devices are inserted into foil bags. A dessicant is placed in the bag with each device. Examples of dessicants which may be useful include silica gel, bentonite, borax, Anhydrone®, magnesium perchlorate, barium oxide, activated alumina, anhydrous calcium chloride, anhydrous calcium sulfate, titanium silicate, anhydrous calcium oxide, and anhydrous magnesium oxide, magnesium sulfate, and Dryrite®, among others, with or without indicator. The bags are then sealed using a thermal press sealer under a dry gas atmosphere, preferably without oxygen, and stored for a designated shelf life.

Cartridge Manufacture

Details are provided for manufacture of a microfluidic cartridge for PCR, but the methods and formulations provided are generally applicable to nucleic acid amplification by both thermocycling and isothermal means and to nucleic acid assays in general where use of on-board dry reagents is contemplated.

Microfluidic cartridges are made with plastic bodies by a process of building up layers.

Each cartridge can be formed of a pair of members or layers glued or fused together, or of a plurality of layers glued or fused together. The term "layer" refers to any of one or more generally planar solid substrate members or glue layers comprising a cartridge; "layers" also includes individual sheets, roll stock, and any molded body members formed as generally planar members. Layers may be joined with pressure sensitive adhesive (PSA) or thermal adhesive. Alternatively, they may be fused under pressure with heat, solvent, or by ultrasonic welding. The number of layers in the device will be dependent on the required functionalities and the fabrication process is chosen.

Channels and chambers formed in the layers become conduits for liquid when enclosed by subsequent layers joined as a stack. These cartridges thus lend themselves to manufacture by stacking of sheets or from multiple rolls laid upon each other as they are fed from multiple feed reels, such as in a roll-to-roll process. The individual channels and chambers are cut, embossed or molded in the layers by one of a variety of processes. Fabrication methods include laser stenciling, lamination, embossing, stamping, injection molding, masking, etching, photocatalyzed stereolithography, soft lithography, and so forth, or any combination of the above.

Plastic is a preferred material for building microfluidic devices of the present invention. Plastics which may be used include olefins, cyclic polyolefins, cyclic olefin copolymers, polyesters, polyethylene terephthalate, polybutylene terephthalate, polystyrenes, polycarbonates, polypropylene, polyethylene, polyurethane, polyether sulfone, polyvinyl chloride, polyvinyl acetate, polyamides, polyimides, polyacrylate, polymethylmethacrylate (PMMA), polytetrafluoroethylenes, polydimethylsiloxane (PDMS), polysilane, cellulose triacetate, thermoplastics in general, and so forth. Composites and copolymers are also frequently used. The knowledge to select plastics or other solid substrates and conventional adhesives is widely known in related arts.

Design of the microfluidic works of the cartridge, where the works are hydraulic networks of channels, chambers, valves, pumps and other microfluidic features, optionally controlled by an overlay of a pneumatic network operatively connected to the hydraulic network through elastic diaphragms, may be simple or complex, but includes provision for insertion of a sample into a sample inlet port and provision for venting as liquid moves through the works. The sample inlet port and vent are fluidly connected by a system of channels and chambers in series or in parallel, where the chambers or channels have an upstream fluid path joined to the sample inlet port and a downstream fluid path joined to the vent.

Enclosed within the internal chambers or channels is at least one vitrified gel reagent spot assembled therein by:

a) combining a first reagent with a printing and stabilizing solution, and printing a droplet of the first printing and stabilizing solution in the chamber or channel and briefly drying the droplet to a hydrated gel state, thereby forming a first gel reagent spot therein;

b) optionally combining a second reagent with a second printing and stabilizing solution, printing a droplet of the second printing and stabilizing solution in the chamber or channel and briefly drying the droplet to a hydrated gel state, thereby forming a second gel reagent spot therein;

c) optionally continuing as in step b until a plurality of on-board gel reagent spots are spotted therein;

d) enclosing the chamber or channel in the plastic body by laminating, gluing, ultrasonically welding, or otherwise attaching a cover or covers thereover;

e) then sealing the microfluidic cartridge with enclosed gel reagent spot or spots in a gas tight pouch under a dry atmosphere with a dessicant, the dessicant further vitrifying the gel reagent spot or spots during storage, thereby forming a vitrified gel spot or spots, the microfluidic cartridge having an extended shelf life at room temperature without need of lyophilization or frozen storage and containing all on-board reagents required for a molecular diagnostic assay.

In this way it is made possible to enclose the dry reagent spots within the microfluidic cartridge at an intermediate step in the manufacturing process. Using this method, sheets of microfluidic cartridges can be made in a continuous or semi-continuous process from roll stock, as illustrated in FIG. 1. Here, eight individually detachable microfluidic cartridges are shown formed as a single production unit (1). The precise number is immaterial, and 48 or 60 or 200 cartridges may be made simultaneously. In the final step of the process, the individual cartridges (2) are separated from each other and packaged in foil pouches with dessicant as described above.

By using automated reagent printers such as the BioDot AD1500 with BioDot Plus Dispenser (Biodot, Irvine Calif.) and X-Y-Z head control, rapid automated deposition of droplets on a base or underlayer of a sheet is achieved. By using multiple heads in series, a pattern of droplets composed of different reagents can be repeated across a sheet. Optionally, individual microfluidic cartridges of the sheet may be printed with different reagents. Printing heads can be contacting or non-contacting.

Turning now to FIG. 2, the printing process is described in more detail. By way of example, in FIG. 2A, a plastic underlayer (20) with cutouts for the bottom wells of channels and chambers forming a PCR amplification subcircuit is shown. The wells of the channels and chambers at this stage are often discontinuous to allow for the placement of vias and valves in subsequent layers. In this schematic representation, four chambers are shown as receiving four reagent spots (black circles), each applied as a liquid that rapidly gels under ambient conditions. Spot 1 (21) contains a fluorescent probe used to detect amplicon products of the amplification. Spot 2 (22) contains an amount of TAQ polymerase, dNTPs, buffer and magnesium salt effective in amplifying the target in a stabilizing gel matrix. Spot 3 (23) contains a primer pair in a liquid droplet. Spot 4 (24) is optional and contains reverse transcriptase, dNTPs, and buffer in a formulation effective in synthesizing a cDNA from an RNA template. Each spot is formulated in a printable matrix that sets to a gel quickly after spotting, and then will dry to a composite gel or glass for stabilizing the reagents over the shelf life of the cartridge. The final drying process, which removes excess hydration water from each spot, takes place in a foil pouch where is provided a quantity of dessicant. Each spot is formulated to rapidly rehydrate when fluid, generally a biological sample, or an eluate, extract or filtrate of a biological sample is introduced at the sample inlet (bottom).

In FIG. 2B, all four reagent spots (open circles) are in a vitrified gel state. The cartridge body (25) is fully assembled by addition of a stack of overlayers onto the underlayer where the spots were printed. Pneumatic diaphragms have also been placed over the valves and over the annealing chamber as required, along with pneumatic control lines extending to an external interface (not shown). In use, a nucleic acid extract entering at the bottom of the cartridge is admitted through a first valve (26) and enters the chamber containing reverse transcriptase and dNTPs in a rapid hydration matrix (spot 24). The channel is vented (29). An incubation follows in which any RNA target is converted to a double stranded duplex which is then suitable for PCR. In a second step of the amplification, a second valve (27) is opened and the sample fluid is advanced into the annealing chamber (15). Here a pair of primers specific for the target nucleic acid sequence have been printed in a vitreous matrix (spot 23) which dissolves into the sample rapidly. The sample is then advanced into the melting chamber (16) and contacted with TAQ polymerase and a modified "master mix" vitrified in a gel matrix (spot 22) at a temperature above the melting temperature of a DNA duplex having the target sequence. The sample is then flowed with reciprocating action (propulsed by the diaphragm 17 forming the roof of the annealing chamber) between the melting chamber and the annealing chamber, each thermocycle resulting in amplification of the target sequence and progressive doubling of the amount of an amplicon product. After a defined number of thermocycles in the paired amplification chambers (18), any amplicon is then detected by flowing the product through a third valve (28) and into the detection chamber (19) and contacted with Spot 1 (21), which contains a fluorescent probe in a glassy or gel matrix. Following rehydration and hybridization of the probe, the sample can be interrogated for the presence of amplicon by fluorescence spectroscopy. An optical window is provided over the detection chamber for this purpose. After the assay result has been read and recorded, the microfluidic cartridge may be removed and discarded.

While the above description is an overview, and the cartridges of this construction are not limited to PCR and thermocycling with reciprocating flow as shown, the above example provides a clear and concise picture of the need for an intermediate step in the manufacturing process of the cartridges prior to final assembly. Following printing, the gel spots are sealed within a plastic body by subsequent lamination, welding or gluing steps, and have no communication with the outside of the body except via the small vent hole (29) and sample inlet. Subsequent freezing of the plastic body and application of vacuum, as required for lyophilization, is likely to disrupt or thermally strain the laminated structure and could also occlude the optical viewing window. Moreover, dusts and fines formed during lyophization are likely to redistribute through the microfluidic workings during release of vacuum, thus contaminating, for example, a first assay pathway specific for a particular target with a primer specific for a second target. Similarly, a positive control template in one channel could be inadvertently introduced into an assay channel intended for a sample or a negative control, resulting in a quality control problem of major proportions. Application of high vacuum after the manufacturing process will also damage elastic diaphragms put in place in the cartridge body. Thus it is difficult or even impossible to imagine how lyophilization could be adapted to a manufacturing process for microfluidic cards having on-board reagents enclosed within the internal channels and chambers, like putting a ship in a bottle.

Use of the gel spots of the inventive compositions and methods is much more elegant and reliable than coating all the reagents with paraffin and melting the paraffin to start the reaction, as has been proposed by Barlag (WO 2006/042838). Gel spots reliably avoid the problems of dust and fines associated with lyophilized, tabletted, or reagent spheres as proposed by others. And precision dispensing of dust, tablets or the lyophilized reagent spheres of the prior art is technically difficult or impossible given the fine dimensions of the target chambers or channels on the card sheets, and the handling required during subsequent processing assuredly would disturb and redistribute those contents, again compounding problems of quality control.

Mere drying is not an acceptable alternative. Numerous studies have shown that many biological reagents do not withstand drying in the absence of a suitable matrix. A suitable matrix must be first discovered by a process of trial and error, upon which much work has been expended, of times without success. TAQ polymerase is one such example. No method for mere drying of TAQ polymerase has ever resulted in a rehydratable solid having activity 6, 3, 2 or even 1 month following drying.

According to the invention, liquid reagent in a gellable matrix is first dispensed onto various surfaces of the microfluidic cartridges, where it is gelled so as to not interfere with subsequent steps of assembly. The gellable matrix is a glass-precursor and subsequent to manufacture of the cartridge is then dewatered further over a period of several days or weeks. Any layer of the cartridge forming a surface accessible to the printing head is a candidate for spotting. As shown in FIG. 3A through D, the roof and floor of a chamber or channel may be spotted with vitrified gel reagent spots (31a-e) in various configurations. Optionally the spot may be permitted to spread from wall to wall in the chamber, or may be confined to a more discrete spot on either the roof or the floor of the chamber. A spot applied on one layer and a spot applied on another layer may be brought into proximity if desired by mating the one spot on the roof of a chamber with the other spot on the floor of the chamber as the layers are stacked.

As can be seen, the method of assembly relies on formulation of the reagents to achieve the desired ends: stability of storage for a commercially acceptable shelf life, precision handling with automated dispensers, rapid gellification to prevent inadvertent mobilization of the reagent on the cartridge during final assembly, slow vitrification in situ under the influence of a dessicant sealed in a gas tight packet or pouch with the microfluidic cartridge, and finally, rapid rehydration and reagent activation in a biological sample or derivative fluid thereof. Formulation is thus an important consideration in adapting a reagent to the microfluidic cartridges having enclosed vitrified gel reagent spots of the invention.

In another embodiment of a microfluidic cartridge of the invention, as contrasted with that described in FIG. 2, the configuration and spotting of reagents may be adapted for Peltier-type PCR or for isothermal amplification. In a Peltier amplification protocol, a single chamber is contacted with a reversible heating and cooling source and a heat exchange membrane (for example as described in U.S. patent application Ser. No. 10/862,826, co-assigned) so that the temperature in the chamber may be thermally cycled between a denaturing temperate and an annealing temperature, with an optional dwell time for strand extension in between. This arrangement eliminates the need for moving the amplification mixture during thermocycling.

Figure 4A:
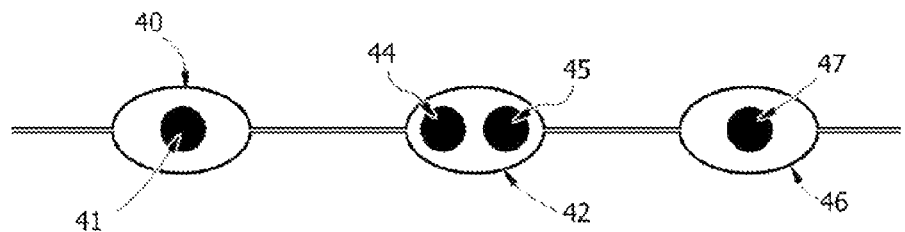
FIGS. 4A through D are schematic representations of alternative configurations of a microfluidic cartridge with on-board reagents and Peltier-type thermocycling capability.

Turning now to FIG. 4A, a Peltier-driven PCR configuration for a microfluidic cartridge with on-board printed reagents is shown. It is assumed (leftmost chamber 40) that reverse transcriptase is provided as a vitrified gel reagent spot (41) and that a target RNA extract is first treated to form a cDNA copy. dNTPs and necessary primers are also provided if needed. In a central chamber, a "Peltier amplification chamber" (42), the sample material is first used to dissolve two reagents spots, a TAQ polymerase reagent spot (43) and a spot containing primers (44). The TAQ polymerase spot may contain necessary cofactors such as added magnesium salt, dNTPs, KCl and a dry buffer. Thermocycling is then conducted in the single chamber while the sample remains stationary. After a requisite number of cycles, the products of the amplification reaction are moved to a detection chamber (46) where the liquid dissolves a vitrified probe in a reagent spot (47). After hybridization, any amplicons in the reaction mixture are detected, for example by fluoroscopy through an optical window mounted above the detection chamber. The detection chamber may include a separate heating block useful for ramping temperature in order to determining melting curves for FRET detection complexes, for example.

Figure 4B:
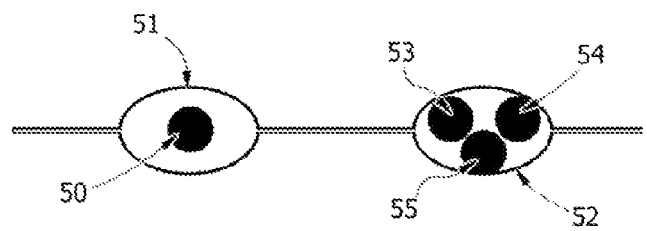

In a second example, as illustrated in FIG. 4B, a reagent spot (50) containing a reverse transcriptase optionally is again used (in reverse transcriptase chamber 51) to convert any RNA to DNA template suitable for PCR. RNA is of interest here in a variety of microbiological or virological diagnostic assays. The sample is then propelled to the rightmost chamber (52), a combined Peltier amplification and detection chamber, which contains three vitrified gel reagent spots. The spots dissolve almost instantaneously and consist of a TAQ polymerase vitrified gel reagent spot (53) with cofactors, a primer reagent spot (54), and a probe reagent spot (55). In this way, a full reagent load required for amplification and simultaneous detection of amplicon is accomplished. When it is desired to effect real time PCR, the probe is necessarily in the amplification chamber. This is the case whether either Peltier or separate heating zones previously discussed (FIG. 2) for amplification are physically separated. The amplification and detection chamber may thus be a dual use chamber and is optionally fitted both with a heating means for cycling temperature and a detection means for monitoring fluorescence, as illustrated here.

Figure 4C:
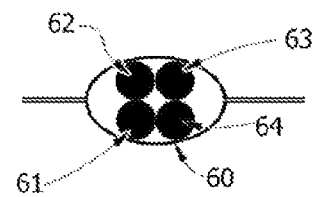

FIG. 4C shows that the assembly of vitrified gel reagent spots in microfluidic chambers can be compacted, for example where all reagents for PCR and detection of an RNA target are printed in a single chamber. Shown are a reverse transcriptase reagent spot (61), a TAQ polymerase reagent spot (62), a primers reagent spot (63), and a probe reagent spot (64) in a PCR detection chamber (60). Clearly DNA targets may be detected without the use of reverse transcriptase.

Figure 4D:
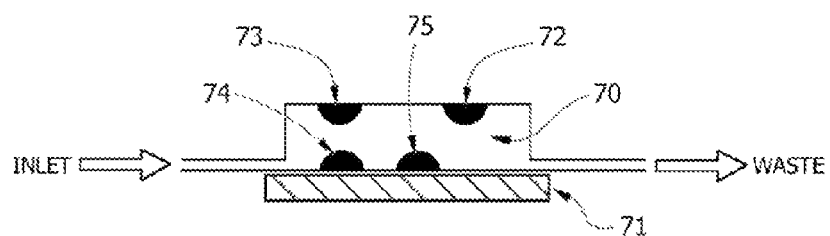

The configuration of gel spots is shown in more detail in FIG. 4D, where a cross-sectional view is shown. Here the enzymes TAQ polymerase and reverse transcriptase are spotted (72,73) on the roof of the chamber (70), out of direct contact with the heating block (71), which may be activated before sample is introduced through the inlet at the left. Primers (74) and probes (75) are spotted on the floor of the chamber. Prior to assembly, the roof and floor substrate layers are open and accessible for printing, so that the final assembly product contains the reagents inside the chamber. By using amorphous vitrified gel composites in the spotting matrix, rapid dissolution is achieved in total reaction volumes typically less than 20 uL, where buffer and salt concentrations are adjusted to be optimal for each reaction. The heating block contacts the amplification chamber through a thin heat exchange membrane and happily, promotes reagent mixing.

As shown, reagents can be spotted in a single chamber or in multiple chambers. Various spot configurations may be employed. Spots may be placed side by side or separated so that some spots are on one substrate layer facing the chamber and other spots are on another substrate layer facing the chamber, mutatis mutandi. In a preferred configuration, a separate detection chamber may be provided, and probe or probes spotted in the detection chamber. During manufacture, spotting of some reagents to one layer of a cartridge and other reagents to another layer is readily accommodated, so that each individual channel of the cartridge can be provided with a unique pattern of individual reagents tailored to the particular assay application. In this way, a panel of assays may be performed on a single cartridge. Both simplex and multiplex reactions may be performed. Sometimes the probes are provided in asymmetric proportions, as is useful in asymmetric PCR. The forward and reverse probes may be mixed together and spotted individually, or they may be spotted separately. Because the spots gel rapidly, in some cases the spots may be stacked on each other or allowed to touch. Configurations for nested PCR are also contemplated using the flexibility inherent in the system. Both spotting geometries as illustrated in FIG. 3 and channel or chamber geometries as illustrated in FIG. 2 may be varied to meet application requirements.

Formulation

Figure 5:
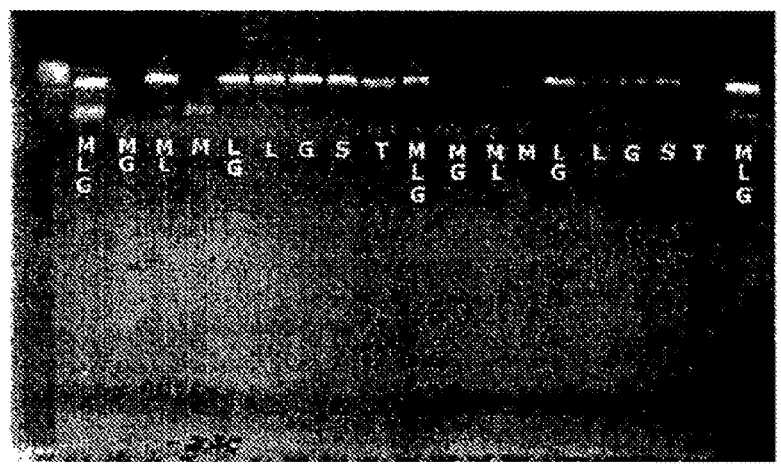
FIG. 5 is a reproduction of a gel of the prior art demonstrating PCR amplification products in various dehydrated reaction mixtures. The figure is reproduced from the declaration of A Madejón (FIG. 1, top panel) of record in the file wrapper of U.S. patent application Ser. No. 10/292,848.
Figure 6:
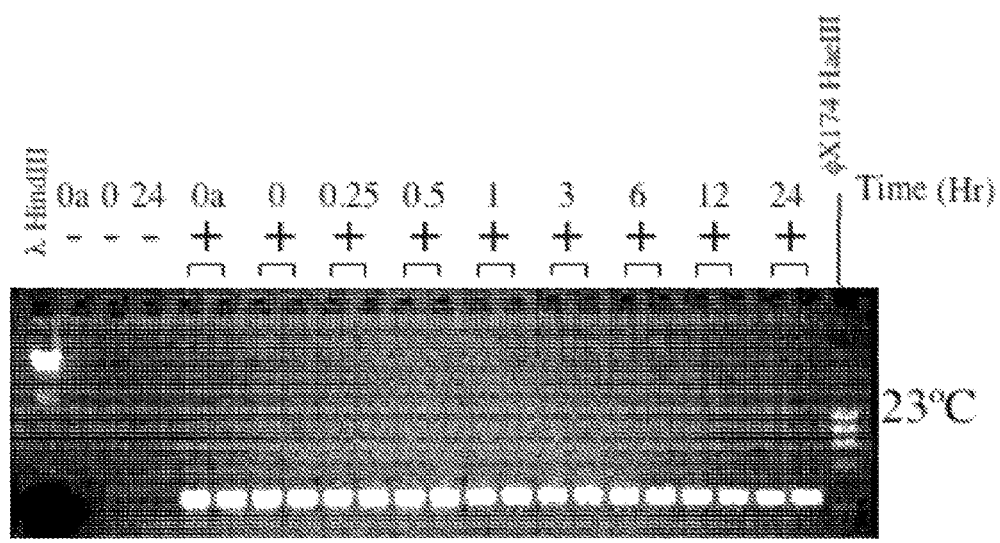
FIG. 6 is a reproduction of a gel of the prior art demonstrating PCR amplification products following storage of TAQ reagent solutions overnight.

We turn now to formulation of the gel reagent spots, which must stabilize the biological reagents contained therein, must gel rapidly during the assembly, and permit progressive vitrification in a post-assembly step, and must be readily rehydrated. TAQ polymerase is again chosen as an example for illustrating the considerations which are given to formulating a reagent for use in the manufacture of the inventive microfluidic cartridges. However these general considerations would also apply to gel stabilization of DNA polymerase used in NASBA, and so forth. FIGS. 5 and 6 are representative of the prior art, and are discussed in the Background (above).

In order amplify a target nucleic acid sequence by PCR months after manufacture of a microfluidic device with on-board with reagents, an efficacious level of TAQ activity must be preserved during storage. Conditions for room temperature storage may be modified to prevent fluctuations in humidity by packaging the devices in sealed foil-lined bags with dessicant. After spotting the TAQ reagent in a buffered mixture with a glass lyoprotectant precursor and excipients onto the devices, the devices are sealed in the bags before full drying is achieved. At this stage the spots are gel-like in consistency. Following sealing in the bag, vitrification continues by a transfer of bound water from the reagent spot to the dessicant. By selection of a compatible glass/excipient composition, this method yields storage stable TAQ assembled in a self-contained microfluidic device which requires only addition of sample to run an assay.

Following a study of several hundred combinations of sugar, co-lyoprotectants, excipients, surfactants and carrier proteins, trehalose and melezitose were selected for further study. We reasoned that an enzyme adapted for activity in a high temperature environment is likely to have a high $T_d$, as evidenced by a $V_{max}$ for many TAQ polymerases around 75° C., and to best preserve that native state, should be coupled in the vitrified state with a glass having a relatively high $T_g$. We also recognized that other excipients such as surfactants may be needed to stabilize the highly folded structure of TAQ during dry storage and to prevent loss of activity due to interfacial denaturation.

Trehalose is a disaccharide composed of two glucose molecules bound by an α,α-1,1 linkage. Since the reducing end of the glucosyl residues are connected with each other, trehalose has no reducing power. Trehalose is widely distributed in nature and protects organisms against various stresses, such as dryness, freezing, and osmopressure. Anhydrobiotic organisms such as brine shrimp and certain nematodes, which resist dessication, are able to tolerate the lack of water because of their high trehalose content; the trehalose playing a key role in stabilizing membranes and other macromolecular assemblies under extreme environmental conditions. Trehalose also has a higher glass transition temperature compared to other disaccharides and has a long history as a stabilizer in dessicated products (see for example Crowe JH et al, 1984, Preservation of membranes in anhydrobiotic organisms the role of trehalose, Science 223:701-703; U.S. Pat. Nos. 4,457,916, 4,206,200, and 4,762,857, and UK Patent GB 2009198), for which is believed to be superior to sucrose. Trehalose is widely believed to be superior to all other lyoprotectants (Colaco C et al, 1992, Extraordinary stability of enzymes dried in trehalose: simplified molecular biology, Bio/Technology 10:1007-11).

Melezitose (α-D-Glucopyranosyl-[1→3]-β-D-Fructofuranosyl-[2→1]-α-D-Glucopyranoside) hydrate is trisaccharide comprised of 2 glucose molecules and 1 fructose molecule with a molecular weight of 504.44 Da in the dry state. It is produced by many plant sap eating insects, including aphids and whiteflies. Melezitose is beneficial to the insects, as it reduces osmotic stress by reducing intracellular water potential as a storage carbohydrate. It is also widely known to function as a cryoprotectant and is used for frozen storage of a wide variety of mammalian cells because of its low osmolarity. Hydrolysis releases glucose and turanose, but the trisaccharide itself is non-reducing and is relatively resistant to Maillard browning. The glass transition temperature of melezitose is higher than that of disaccharides.

Comparative values for $T_g$ are shown in the following Table I:

TABLE I

|  | Tg (° K) | Tg (° C.) |
| --- | --- | --- |
| Glycerol | 180.0 | −93.2 |
| Sucrose | 348.0 | 74.9 |

TABLE I-continued

|  | Tg (° K) | Tg (° C.) |
| --- | --- | --- |
| Raffinose (pentahydrate) | 352.7 | 79.6 |
| Raffinose (trihydrate) | 358.4 | 85.3 |
| Raffinose (anhydrous) | 376.4 | 103.3 |
| Trehalose (dehydrate) | 305.2 | 32.0 |
| Trehalose (anhydrous) | 352.2 | 79.0 |
| Stachyose (anhydrous) | 405.1 | 132.0 |
| Melezitose (anhydrous) | 433.1 | 160.0 |

The value for the $T_g$ of melezitose was obtained from "Mollmann, S H et al, 2006, The stability of insulin in solid formulations containing melezitose and starch. Drug Dev Indust Pharmacy 32:765-778. Other values were obtained from Green J L and C A Angell, 1989, Phase relations and vitrification in saccharide-water solutions and the trehalose anomaly, J Phys Chem 93:2880-82; Kajiwara K and F Franks, 1997, Crystalline and amorphous phases in the binary system water-raffinose, J Chem Soc Faraday Trans 93:1779-1783; Slade L and H Levine. 1988. Non-equilibrium behavior of small carbohydrate-water systems, Pure & Appl Chem 60:1841-64; and Heldman D R and D B Lund, 2006, Handbook of Food Engineering (2nd ed) CRC Press, Boca Raton Fla. Not all sources are in firm agreement; however it is generally agreed that $T_g$ increases with molecular weight and decreases with water of hydration.

Beginning with a hydrated sugar ensures that the $T_g$ is initially low and the formulation is a liquid, but upon dessication, $T_g$ will increase and will approach a value where room temperature storage is in the form of an amorphous glass. During this process, it is desirable that crystallization of anhydrous sugar not occur. Co-solvent excipients are useful to prevent undesirable crystallization and to more selectively associate with the TAQ polymerase, as is determined by a process of trial and error.

Formulation 1 consists of (as final concentrations in water) 1.5% melezitose hydrate, 0.005% Polyox WSR-301 (Amerchol Corp, Piscataway N.Y.), 0.1 mg/mL BSA and 10 Units TAQ polymerase in an aqueous solution. Following preparation of the TAQ solution stock with stabilizers, the clear gel precursor solution was applied in 3 uL spots to the internal surfaces of a plastic microfluidic device or card. Primers and probes were stored separately. The spots were allowed to dry for about 10 minutes or less at controlled room temperature and the plastic devices were then sealed in air-tight pouches with dessicant sachets and stored at controlled room temperature. Polyox WSR-301 is a long-chain polyoxyethylene glycol (4 MDa molecular weight, also termed "PEG-90M"). Molecular biology grade water was used for all formulations. While bovine serum albumin is a preferred protein carrier, fish gelatin may also be used in the method. Betaine or lysine may also be used.

The following formulations were prepared for side-by-side comparison in a two month stability study: Formulation 2 was compounded as 1.5% trehalose, 0.005% Polyox WSR-301, 0.1 mg/mL BSA and 10 Units TAQ polymerase. Formulation 3 contained 1.5% melezitose hydrate, 0.1% Ficoll® 400, 0.1 mg/mL BSA. Formulation 4 contained 1.5% trehalose, 0.1% Fluorosurfactant FC4430 (3M Corp), and 0.1 mg/mL BSA. Formulation 5 contained 1.5% trehalose, 0.1% PEG8000, and 0.1 mg/mL BSA. Formulation 6 contained 1.5% trehalose, 0.1% Cellulose Gum 7LF, and 0.1 mg/mL BSA. Formulation 7 contained 1.5% lactitol, 0.005% Polyox WSR-301, and 0.1 mg/mL BSA. TAQ used in these experiments was EconoTaq® Plus (Lucigen Corp, Middleton Wis.) formulated at 10 U/uL.

All formulations were mixed with a standard quantity of TAQ polymerase and spotted on a plastic surface for testing. Following spotting, the gel composite precursor spots were allowed to set briefly for about 10 minutes and then closed and sealed in a moisture-proof, gas-tight pouch along with an excess quantity of a dessicant to progressively vitrify the gel spots. Typically, silica gel or bentonite with indicator is used. The pouches were thermally sealed under a dry, inert atmosphere.

Figure 7:
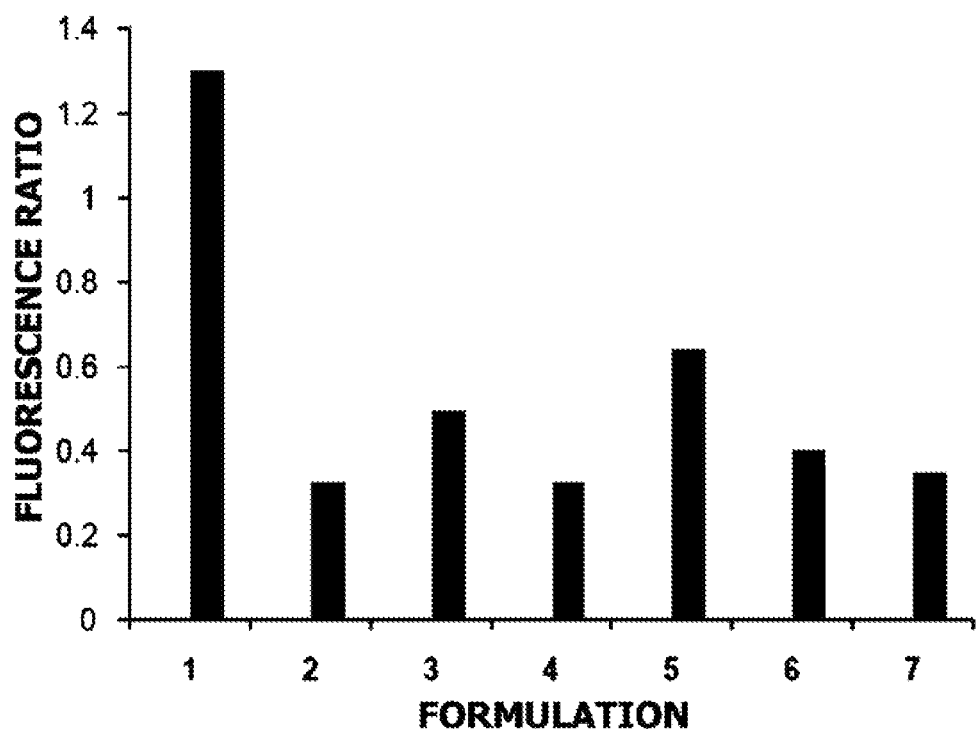
FIG. 7 is a bar graph comparing formulations of TAQ following dry storage for two months.
Figure 8:
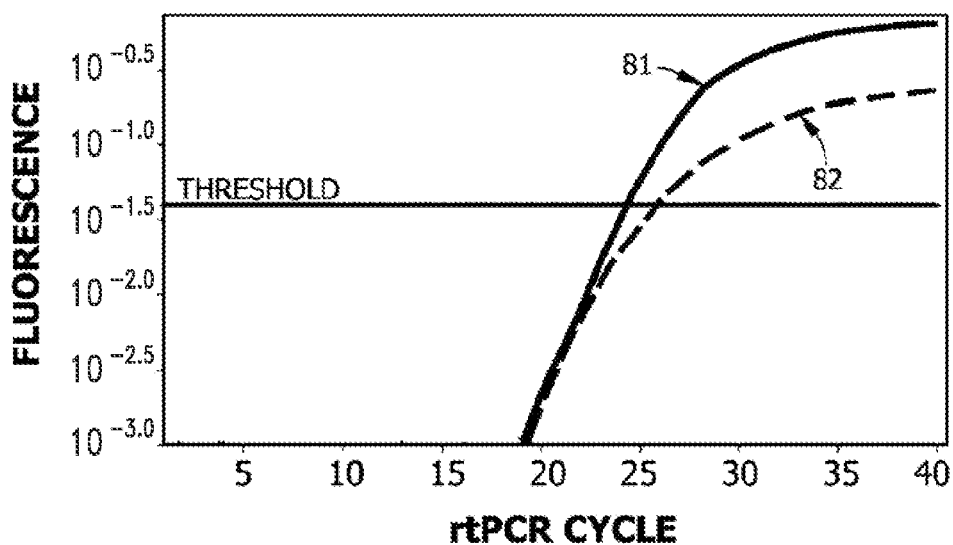
FIG. 8 is a rtPCR curve showing TAQ activity of a dry mixture following rehydration versus a freshly prepared wet reaction mixture (undried).
Figure 9:
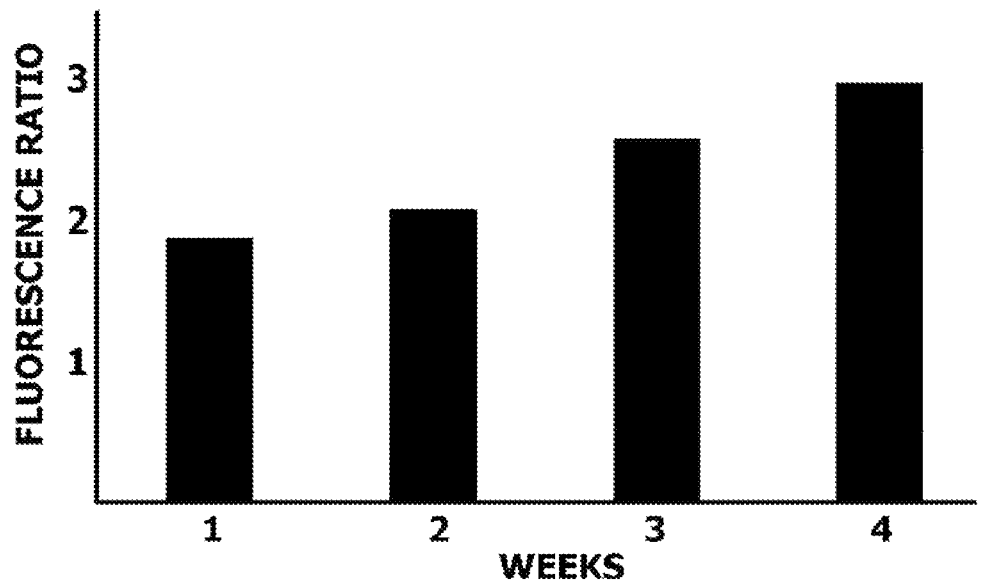
FIG. 9 is a bar graph showing increase in TAQ potency over commercially supplied stock during progressive vitrification in a melezitose glass at room temperature.
Figure 10:
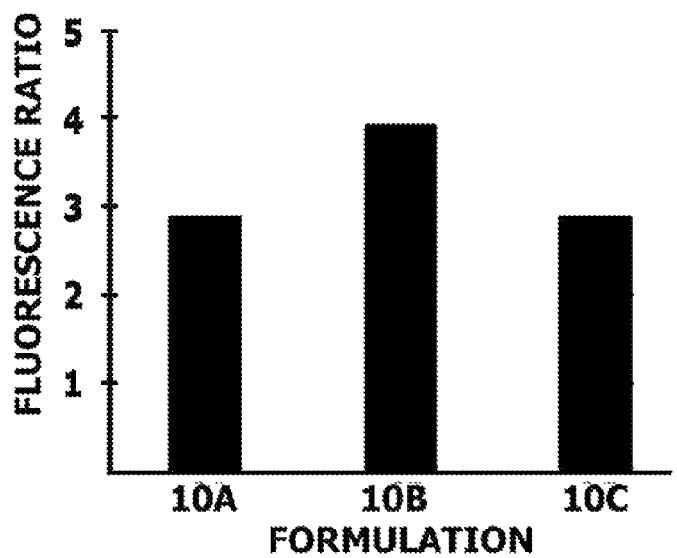
FIG. 10 is a bar graph showing TAQ potency following vitreous storage in melezitose versus trehalose with selected excipients.
Figure 11:
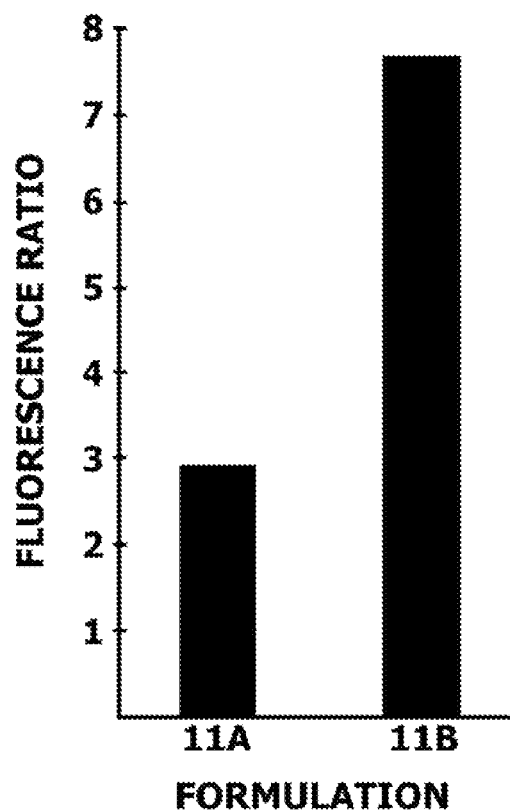
FIG. 11 shows TAQ potency following vitreous storage with excipient fluorosurfactant FC-4430 (3M Corp).

The data at 2 months stability storage testing are reported in FIG. 7. The results are shown as fluorescence ratio normalized for activity of a freshly mixed "wet" amplification performed without drying. As can be seen, most formulations failed to maintain full potency. However, Formulation 1, the melezitose/Polyox WSR-301/BSA gel based formulation is seen to outperform the standard wet amplification mixture by a factor of 1.3 after 2 months storage at room temperature. In contrast, melezitose hydrate prepared with Ficoll 400 was not convincingly stable after two months, and trehalose formulated with Polyox WSR-301 or a variety of alternate excipients similarly failed to provide a suitable storage stability period.

In these studies, a *Salmonella paratyphi* primer pair having 5000 copies/reaction was used for amplification. The rehydrated complete amplification mixtures were thermocycled and detection completed using a molecular beacon or FRET probe. Ct and fluorescence yield ratio were measured for each reaction. A sample real time PCR amplification curve, comparing melezitose formulation 1 after extended dry storage and a fresh wet reaction is shown in FIG. 8. The solid curve (81) is the activity of the dried TAQ reagent, the dotted line curve (82) is the activity of the standard wet TAQ reaction mixture.

In FIG. 9, the behavior of the melezitose of Formulation 1 as a function of storage stability period is examined further. It can be seen that during the initial period of processing, TAQ polymerase activity steadily increases over a 4 week period. The fluorescence ratio again is the ratio of fluorescence achieved in real time PCR. We interpret this result as not artifactual; it may represent recruitment of native state conformers from a stock solution of TAQ polymerase molecules damaged during the manufacturing and storage process. While not bound by theory, it is thought that commercially available frozen preparations contain a percentage of freeze-denatured TAQ molecules, mixtures of conformers, some as native state conformation and some not, some variants less active than others, and the stabilization procedure has the effect of repairing the conformational state of at least some of the damaged molecules.

FIG. 10 compares three formulations in amplifications with a different primer system. Formulations 10A, 10B and 10C are compared, where 10A is equivalent to Formulation 3 above, 10B is equivalent to Formulation 1 above, and 10C is equivalent to formulation 5 above. As can be seen, the formulation containing melezitose 1.5%/0.005% Polyox WSR-301/0.1% BSA is again superior after dry storage by the method of sealing gel spots in gas-tight pouches with dessicant so that a gradual, progressive dewatering of the enzyme is achieved.

FIG. 11 compares a formulation 11A containing trehalose with 0.1% PEG8000 with a formulation 11B containing trehalose with 0.1% Fluorosurfactant FC4430. Surprisingly, the fluorosurfactant had a remarkable effect on fluorescence yield in this 2 week dry storage data.

It has further been found that dry PCR enhancers are of value in microfluidic PCR. Enhancers serve multiple functions, including improving performance of GC-rich DNA substrates as templates and increasing specificity and yield. Various amides, sulfoxides, sulfones, and diols are known to improve PCR yield and specificity, often dramatically better than betaine. DMSO, tetramethylene sulfoxide, formamide, 2-pyrrolidone are examples. Some enhancers, such as n,n-dimethyformamide and DMSO have been used to reduce the temperatures required for thermocycling, which in saline may require heating the solution to near-boiling, with attendant issues of pressure and outgassing. However, enhancers that can be stored in dry form as a composite as a gel or glass are required here.

Enhancers include glass formers of value as co-lyoprotectants. These enhancers include n-formyl morpholine (melting point 23° C.), δ-valerolactam (2-piperidone, melting point 38-40° C.), ε-caprolactam (melting point 69-70° C.), and 1,2-cyclopentanediol (melting point of 54-56° C.). PVP-10 is reported to have a glass transition temperature of 66° C. and PVP-40 a $T_g$ of 99° C. Other glass formers of function in improving PCR include amino acids such as lysine, low molecular weight amides, carbohydrates such as glycogen and inulin, albumins (both HSA and BSA), and a range of sugars as earlier discussed.

EXAMPLES

Example 1

PCR Standard Reaction

As a wet standard reaction, stock frozen TAQ polymerase was added to freshly prepared PCR reagent stock mix according to Table II.

TABLE II

| COMPOSITION | Stock Concentration | Volume of Reaction (uL) | Final Concentration |
|---|---|---|---|
| 100 mM Tris pH 8.0, 500 mM KCl, 15 mM $MgCl_2$ | 10x | 2.0 | 1x |
| $MgCl_2$ | 50 mM | 1.4 | 3.5 mM |
| dNTPs | 10 mM | 0.4 | 0.2 mM |
| Primer/Probe Mix | 20x | 1.0 | 1x |
| TAQ polymerase | 2.5 U/uL | 0.4 | 1 U |
| Std DNA template | | 5.0 | |
| water | | 9.8 | |
| Total Volume | | 20.0 uL | |

The reaction mixture was thermocycled using a Rotor Gene® Q (Qiagen Carlsbad Calif.) thermocycler with rtPCR monitoring. Real time PCR was monitored to obtain crossing threshold (Ct); i.e., the measurement the cycle number at which the increase in fluorescence (and therefore DNA) is exponential and the fluorescence yield ($F_{STD}$). A melt curve was run on all successful amplifications to verify correct amplification of the target amplicon. Endpoint detection may also be used. Optionally, a FRET melting curve may be included to verify the identity of the amplicon.

Example 2

Dry Reagent Assay

Reaction mixes containing TAQ polymerase, lyoprotectant, co-lyoprotectant, and protein carrier or excipient, as well as KCl, $Mg^{2+}$, and dNTPs, where prepared as about a 5× stock and spotted in a microfluidic card or on a plastic surface as 3 uL spots. The spots were allowed to gel at room temperature for about 10 min or less, and then placed in foil bags supplied by Vaporflex Preservation Packaging (LPS Industries, Moonachie, N.J.). To reconstitute, a volume of 15 uL containing target DNA and primers was used.

The reconstituted volume was then amplified in the presence of primers and template in a Rotor Gene®. Ct and fluorescence yield ($F_X$) were measured and compared to the standard, wet mix (above). A fluorescence ratio was calculated ($F_X/F_{STD}$).

Melezitose, trehalose, lactulose and other sugars were obtained from Sigma Chemicals (St Louis Mo.). Polyol WRS301 (also known as "PEG 90M", 1% viscosity 1650-550 cps, 4 MDa MW) is supplied by Amerchol Corp, Piscataway N.Y. Fluorosurfactant FC-4430 was obtained from 3M Corp. Reagents were molecular biology grade where possible.

Example 3

Formulation 1

A formulation for ambient dry storage of TAQ polymerase in a microfluidic device was prepared per Table III. Sugar was added from a 25% solution of melezitose hydrate in water. A stock containing 0.01% Polyol WRS301 as excipient was used in this example.

TABLE III

| COMPOSITION | Stock Concentration | Volume per Reaction (uL) | Concentration per Reaction |
|---|---|---|---|
| 1M Tris pH 8.4, 2.5M KCl | 50x | 0.3 | 20 mM Tris, 50 mM KCl |
| dNTP Mix | 10 mM | 0.3 | 0.2 mM |
| $MgCl_2$ | 1M | 0.15 | 10 mM |
| BSA | 25% | 0.15 | 0.25% |
| Sugar | 25% | .9 | 1.50% |
| Excipient | varies | .15 | varies |
| TAQ polymerase | 10 U/uL | 0.96 | 10 U |
| Total volume on rehydration with target DNA/primer solution | | 15 uL | |

The resulting clear gel composite precursor solution was spotted with a pipet onto a passivated plastic surface (PET) of a microfluidic device. Spots were allowed to set for about 10 min and then sealed in foil bags with dessicant. A chromogenic indicator was used to verify the integrity of the sealed bags during storage. The pouches were heat sealed before storage.

While the above is a complete description of the presently preferred embodiments of the present invention, it is possible to use various alternatives, modifications and equivalents. All of the US patents, US patent application publications, US patent applications, foreign patents, foreign patent applications and non-patent publications referred to in this specification, claimed as priority documents, and/or listed in any Information Data Sheets, are incorporated herein by reference, in their entirety. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A microfluidic cartridge comprising on-board reagents for performing a molecular diagnostic assay, said microfluidic cartridge comprising a body with enclosed microfluidic works having at least one chamber or channel, said chamber or channel having an upstream fluid path joined to a sample inlet port and a downstream fluid path joined to a vent, wherein enclosed within said chamber or channel is at least one vitrified gel reagent spot, the vitrified gel reagent spot comprising:
   a) a DNA polymerase;
   b) one or more excipients comprising a disaccharide or a trisaccharide; and
   c) a fluorosurfactant.

2. The microfluidic cartridge of claim 1, wherein the DNA polymerase is a TAQ polymerase.

3. The microfluidic cartridge of claim 1, wherein the disaccharide is trehalose.

4. The microfluidic cartridge of claim 1, wherein the trisaccharide is melezitose or raffinose.

5. The microfluidic cartridge of claim 1, wherein the one or more excipients further comprises a high molecular weight polyethylene glycol.

6. The microfluidic cartridge of claim 5, wherein the high molecular weight polyethylene glycol has a molecular weight ranging from 0.1 to 5 MDa, inclusive.

7. The microfluidic cartridge of claim 5, wherein the high molecular weight polyethylene glycol is a linear polyethylene glycol.

8. The microfluidic cartridge of claim 1, wherein the one or more excipients further comprises an amino acid.

9. The microfluidic cartridge of claim 1, wherein the one or more excipients further comprises a carrier protein.

10. The microfluidic cartridge of claim 9, wherein the carrier protein is bovine serum albumin or fish gelatin.

11. The microfluidic cartridge of claim 1, wherein the fluorosurfactant is a non-ionic fluoroalkylsurfactant.

12. The microfluidic cartridge of claim 1, wherein the fluorosurfactant is Fluorosurfactant FC-4430.

13. The microfluidic cartridge of claim 1, further comprising a second gel reagent spot comprising a primer or primers.

14. The microfluidic cartridge of claim 1, further comprising one or more additional gel reagent spots, the one or more additional gel reagent spots independently comprising a probe or probes, a reverse transcriptase, an RNA polymerase, nucleotide triphosphates, a nucleic acid template, or a buffer.

15. The microfluidic cartridge of claim 1, wherein the microfluidic works comprises a plurality of chambers or channels fluidly connected as a parallel array of assay pathways between the sample inlet port and the vent, wherein within each assay pathway comprises at least one gel reagent spot therein.

16. The microfluidic cartridge of claim 15, wherein each assay pathway comprises a gel reagent spot comprising at least one unique primer pair.

17. The microfluidic cartridge of claim 15, wherein each assay pathway comprises a gel reagent spot comprising at least one probe.

18. The microfluidic cartridge of claim 15, wherein each assay pathway comprises a gel reagent spot comprising a DNA polymerase and a flourosurfactant.

19. The microfluidic cartridge of claim 1, wherein the vitrified gel reagent spot further comprises a PCR enhancer selected to form a glass at room temperature.

20. The microfluidic cartridge of claim 19, wherein the PCR enhancer is betaine, n-formyl morpholine, δ-valerolactam (2-piperidone), ε-caprolactam, 1,2-cyclopentanediol, PVP-10, PVP-40, or a mixture thereof.

21. The microfluidic cartridge of claim 1, wherein the vitrified gel reagent spot further comprises inulin, cellulose, derivatized cellulose, polyvinylpyrrolidone, lysine, arginine, or a Maillard reaction inhibitor.

22. A kit comprising the microfluidic cartridge of claim 1 individually packaged in a gas tight pouch under a dry atmosphere with a desiccant, and comprising labeling and instructions for use.

\* \* \* \* \*